US011021718B2

(12) United States Patent
Joung et al.

(10) Patent No.: US 11,021,718 B2
(45) Date of Patent: Jun. 1, 2021

(54) METHODS FOR INCREASING EFFICIENCY OF NUCLEASE-INDUCED HOMOLOGY-DIRECTED REPAIR

(71) Applicant: The General Hospital Corporation, Boston, MA (US)

(72) Inventors: J. Keith Joung, Cambridge, MA (US); Benjamin Kleinstiver, Medford, MA (US); Jason Michael Gehrke, Santa Barbara, CA (US); Shengdar Tsai, Memphis, TN (US); James Angstman, Cambridge, MA (US); Rebecca Tayler Cottman, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 253 days.

(21) Appl. No.: 15/516,310

(22) PCT Filed: Oct. 1, 2015

(86) PCT No.: PCT/US2015/053417
§ 371 (c)(1),
(2) Date: Mar. 31, 2017

(87) PCT Pub. No.: WO2016/054326
PCT Pub. Date: Apr. 7, 2016

(65) Prior Publication Data
US 2018/0230494 A1 Aug. 16, 2018

Related U.S. Application Data

(60) Provisional application No. 62/058,456, filed on Oct. 1, 2014.

(51) Int. Cl.
| | |
|---|---|
| *C12N 15/90* | (2006.01) |
| *C12N 9/22* | (2006.01) |
| *C12N 15/11* | (2006.01) |
| *C12N 15/10* | (2006.01) |
| *C12N 15/63* | (2006.01) |

(52) U.S. Cl.
CPC ............. *C12N 15/907* (2013.01); *C12N 9/22* (2013.01); *C12N 15/102* (2013.01); *C12N 15/11* (2013.01); *C12N 15/63* (2013.01); *C07K 2319/00* (2013.01); *C07K 2319/09* (2013.01); *C07K 2319/095* (2013.01); *C07K 2319/80* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | |
|---|---|---|
| 2005/0026157 A1 | 2/2005 | Baltimore et al. |
| 2010/0100977 A1 | 4/2010 | Miyawaki et al. |
| 2011/0301073 A1 | 12/2011 | Gregory et al. |
| 2012/0178647 A1 | 7/2012 | Usui |
| 2012/0276074 A1* | 11/2012 | Scharenberg .......... A61K 38/45 424/94.2 |
| 2013/0253040 A1 | 9/2013 | Miller et al. |
| 2013/0259806 A1 | 10/2013 | Light et al. |
| 2014/0170141 A1 | 6/2014 | Toporik et al. |

FOREIGN PATENT DOCUMENTS

WO WO2014/173955 10/2014

OTHER PUBLICATIONS

Gookin et al., PLoS Biol 2017, 15(9): e2003268 https://doi.org/10.1371/journal.pbio.2003268 (Year: 2017).*
Howden et al., Stem Cell Reports (Sep. 2016) 7(3)508-517 (Year: 2016).*
Gutschner et al., (2016) Cell Reports 14:1555-156 (Year: 2016).*
Gaj et al., Trends in Biotechnology, Jul. 2013, vol. 31, No. 7, 397-405 (Year: 2013).*
International Search Report and Written Opinion dated Feb. 5, 2016 in International Application No. PCT/US2015/053417, 14 pgs.
Kim et al., "Hybrid restriction enzymes: Zinc finger fusions to Fok I cleavage domain," Proc. Natl., Acad. Sci. USA, 93:1156-1160 (1996).
Guilinger et al., "Fusion of catalytically inactive Cas9 to FokI nuclease improves the specificity of genome modification," Nat Biotechnol. 32(6):577-582 (2014).
Li et al., "TAL nucleases (TALNs): hybrid proteins composed of TAL effectors and FokI DNA-cleavage domain," Nucleic Acids Research 39(1):359-372 (2011).
Abe et al., "Visualization of cell cycle in mouse embryos with Fucci2 reporter directed by Rosa26 promoter," Development, Jan. 2013, 140: 237-246.
Barahmand-pour et al., "A role for STAT family transcription factors in myeloid differentiation," Curr. Top. Microbiol. Immunol, 1996, 211:121-128.
Feuerstein et al., "The LIM/ double zinc-finger motif functions as a protein dimerization domain," PNAS, 1994, 91:10655-10659.
Haurwitz et al., "Csy4 relies on an unusual catalytic dyad to position and cleave CRISPR RNA," EMBO J, Jun. 2012, 31(12): 2824-2832.
Ho et al., "Dimeric ligands define a role for transcriptional activation domains in reinitiation," Nature, 1996, 382:822-826.
Hsu et al., "DNA targeting specificity of RNA-guided Cas9 nucleases," Nature Biotechnology, Jul. 2013, 31: 827-832.
Jinek et al., "RNA-programmed genome editing in human cells," eLIFE, Jan. 2013, 2: e00471-1.
Kim et al., "Hybrid restriction enzymes: zinc finger fusions to Fok I cleavage domain," PNAS, Feb. 1996, 93:1156-60.
Klemm et al., "Dimerization as a regulatory mechanism in signal transduction," Annu Rev. Immunol, 1998, 16:569-592.
Lee et al., "RNA—protein analysis using a conditional CRISPR nuclease," PNAS, Apr. 2013, 110(14): 5416-5421.

(Continued)

Primary Examiner — James D Schultz
(74) Attorney, Agent, or Firm — Fish & Richardson P.C.

(57) ABSTRACT

The present invention relates to methods to improve the absolute rate of homology-directed repair (HDR) and/or to improve the relative rate of HDR compared with non-homologous end joining (NHEJ).

14 Claims, 6 Drawing Sheets

Specification includes a Sequence Listing.

(56) References Cited

OTHER PUBLICATIONS

Li et al., "Transcription activator-like effector hybrids for conditional control and rewiring of chromosomal transgene expression," Scientific Reports, 2012, 2:897.
Lin et al., "Enhanced homology-directed human genome engineering by controlled timing of CRISPR/Cas9 delivery," eLIFE, Dec. 2014, 3: 04766.
Maeder et al., "Robust, synergistic regulation of human gene expression using TALE activators," Nat Methods, Mar. 2013, 10(3):243-5.
McCarty et al., "Selective dimerization of a C2H2 zinc finger subfamily," Mol. Cell, Feb. 2003, 11:459-470.
O'Shea et al., "X-ray structure of the GCN4 leucine zipper, a two-stranded, parallel coiled coil," Science, Oct. 1991, 254:539.
Pomerantz et al., "Structure-based design of a dimeric zinc finger protein," Biochemistry, Jan. 1998, 37:965-970.
Rivera-Torres et al., "The Position of DNA Cleavage by TALENs and Cell Synchronization Influences the Frequency of Gene Editing Directed by Single-Stranded Oligonucleotides," PLOS ONE, May 2014, 9: e96483.
Sakaue-Sawano et al., "Drug-induced cell cycle modulation leading to cell-cycle arrest, nuclear mis-segregation, or endoreplication," BMC Cell Biol, Jan. 2011, 12:2.
Sakaue-Sawano et al., "Visualizing spatiotemporal dynamics of multicellular cell-cycle progression," Cell, Feb. 2008, 132:487-98.
Supplementary European Search Report in Application No. 15846033.7, dated Jan. 31, 2018, 8 pages.
Tremblay et al., "Transcription activator-like effector proteins induce the expression of the frataxin gene," Hum Gene Ther, Aug. 2012, 23(8):883-90.
Wang and Pabo, "Dimerization of zinc fingers mediated by peptides evolved in vitro from random sequences," PNAS, Aug. 1999, 96:9568.
Wolfe et al., "Combining structure-based design with phage display to create new Cys(2)His(2) zinc finger dimers," Structure, Jul. 2000, 8: 739-750.
EP Office Action in European Appln. No. 15846033.7, dated Jan. 23, 2019, 10 pages.
EP Office Action in European Appln. No. 15846033.7, dated Dec. 2, 2019, 3 pages.
IL Office Action in Israeli Appln. No. 251432, dated Jan. 14, 2020, 10 pages (with English translation).
PCT International Preliminary Report on Patentability in International Appln. No. PCT/US2009/042061, dated Apr. 13, 2017, 10 pages.
AU Office Action in Australian Application No. 2015324935, dated Dec. 1, 2020, 6 pages.

* cited by examiner

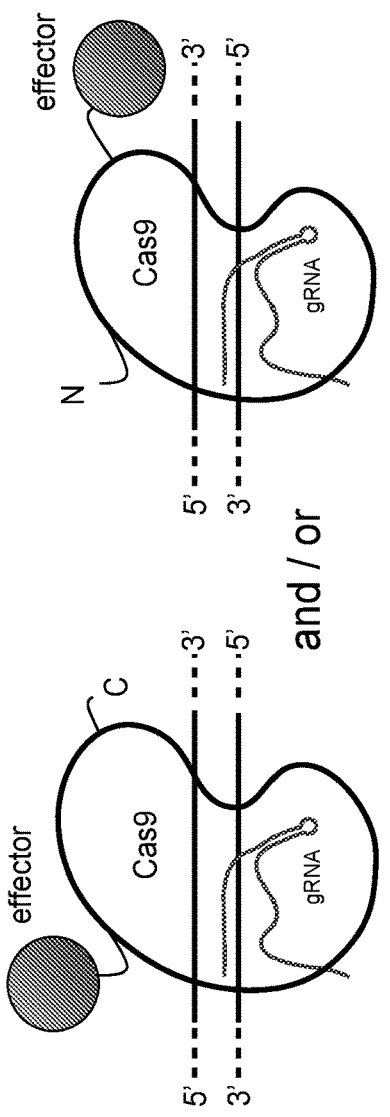
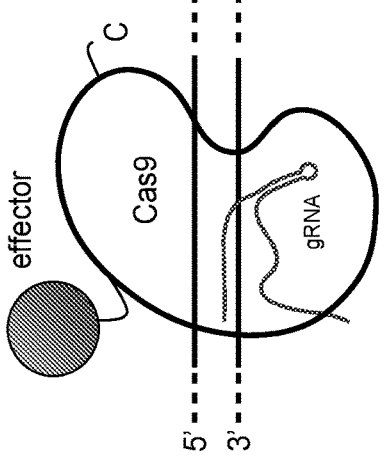
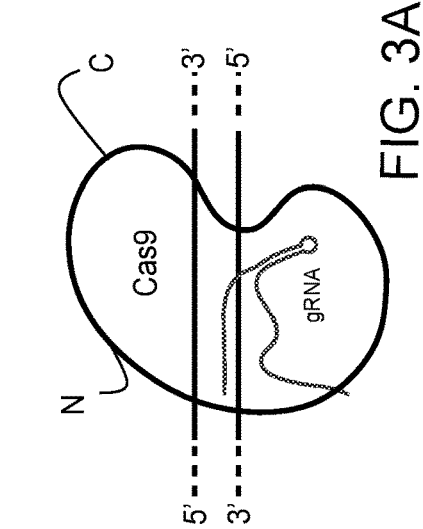
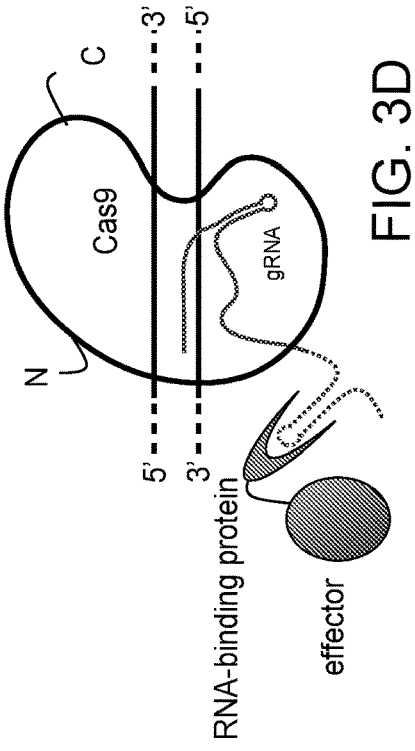
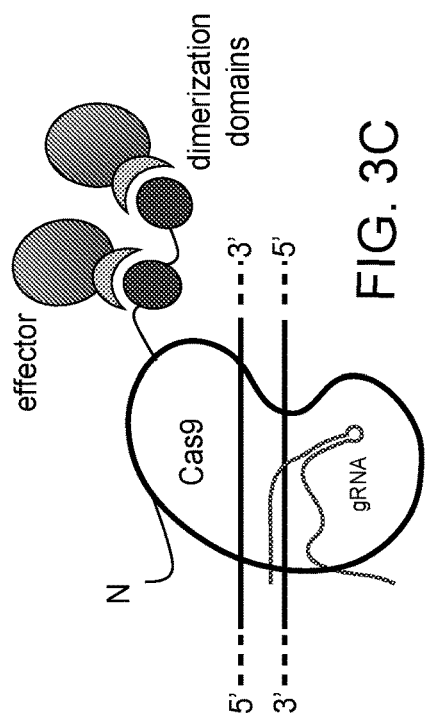
FIG. 3A
FIG. 3B
FIG. 3C
FIG. 3D

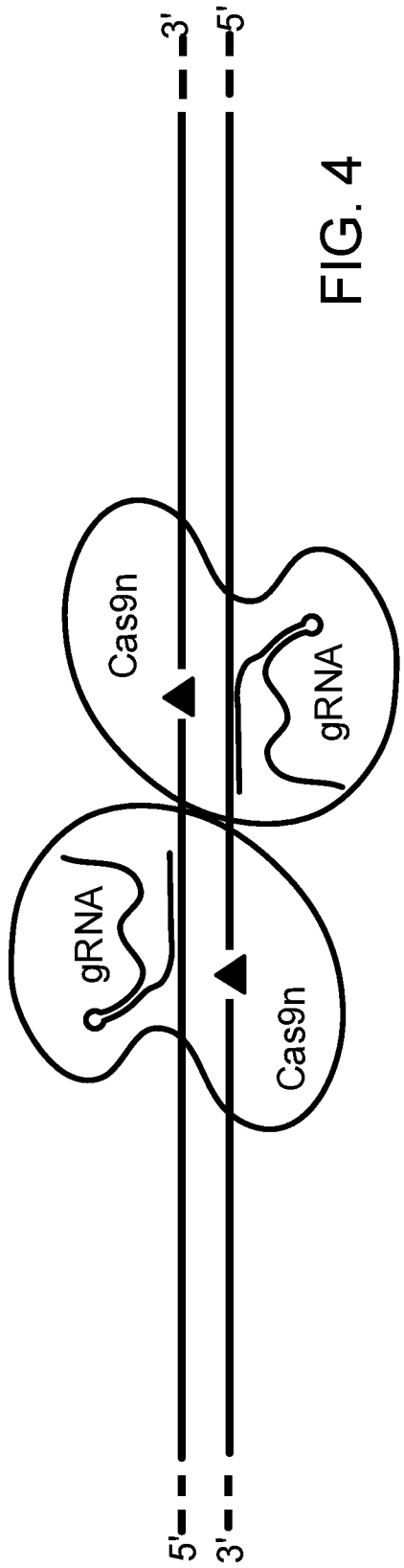
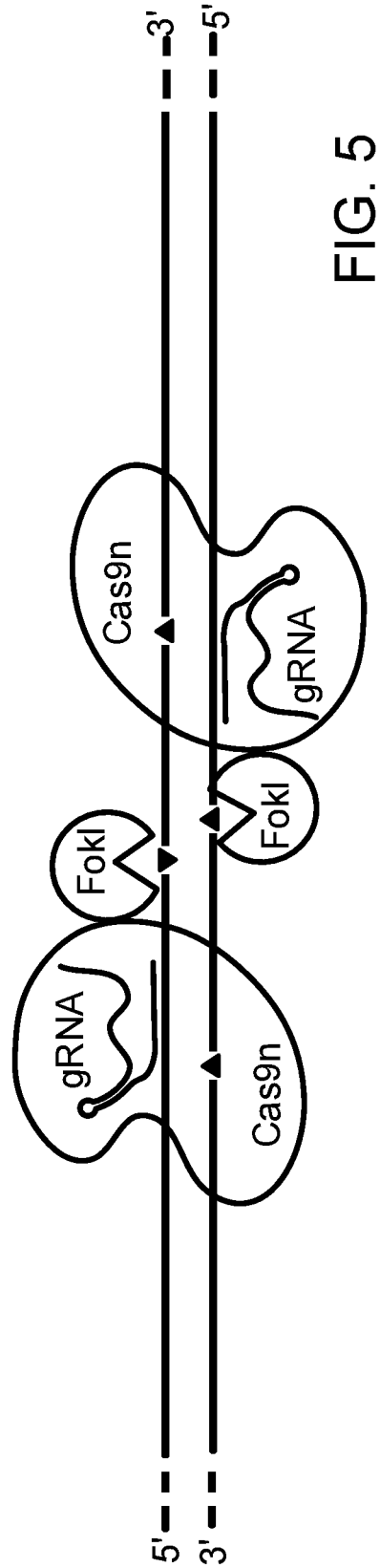

SEQUENCE LISTING

<160> NUMBER OF SEQ ID NOS: 9

<210> SEQ ID NO 1
<211> LENGTH: 708
<212> TYPE: DNA
<213> ORGANISM: Galaxea fascicularis

<400> SEQUENCE: 1

```
atggtgagcg tgatcaagcc cgagatgaag atcaagctgt gcatgagggg caccgtgaac        60
ggccacaact tcgtgatcga gggcgagggc aagggcaacc cctacgaggg cacccagatc       120
ctggacctga acgtgaccga gggcgccccc ctgcccttcg cctacgacat cctgaccacc       180
gtgttccagt acggcaacag ggccttcacc aagtaccccg ccgacatcca ggactacttc       240
aagcagacct tccccgaggg ctaccactgg gagaggagca tgacctacga ggaccagggc       300
atctgcaccg ccaccagcaa catcagcatg aggggcgact gcttcttcta cgacatcagg       360
ttcgacggca ccaacttccc ccccaacggc cccgtgatgc agaagaagac cctgaagtgg       420
gagcccagca ccgagaagat gtacgtggag gacggcgtgc tgaagggcga cgtgaacatg       480
aggctgctgc tggagggcgg cggccactac aggtgcgact tcaagaccac ctacaaggcc       540
aagaaggagg tgaggctgcc cgacgcccac aagatcgacc acaggatcga tcctgaag         600 cacgacaagg actacaacaa ggtgaagctg tacgagaacg ccgtggccag gtactccatg       660
ctgcccagcc aggccaaggg atatccatca cactggcggc cgctcgag                    708
```

<210> SEQ ID NO 2
<211> LENGTH: 236
<212> TYPE: PRT
<213> ORGANISM: Galaxea fascicularis

<400> SEQUENCE: 2

```
Met Val Ser Val Ile Lys Pro Glu Met Lys Ile Lys Leu Cys Met Arg
1               5                   10                  15

Gly Thr Val Asn Gly His Asn Phe Val Ile Glu Gly Glu Gly Lys Gly
            20                  25                  30

Asn Pro Tyr Glu Gly Thr Gln Ile Leu Asp Leu Asn Val Thr Glu Gly
        35                  40                  45

Ala Pro Leu Pro Phe Ala Tyr Asp Ile Leu Thr Thr Val Phe Gln Tyr
    50                  55                  60

Gly Asn Arg Ala Phe Thr Lys Tyr Pro Ala Asp Ile Gln Asp Tyr Phe
65                  70                  75                  80

Lys Gln Thr Phe Pro Glu Gly Tyr His Trp Glu Arg Ser Met Thr Tyr
                85                  90                  95

Glu Asp Gln Gly Ile Cys Thr Ala Thr Ser Asn Ile Ser Met Arg Gly
            100                 105                 110

Asp Cys Phe Phe Tyr Asp Ile Arg Phe Asp Gly Thr Asn Phe Pro Pro
        115                 120                 125

Asn Gly Pro Val Met Gln Lys Lys Thr Leu Lys Trp Glu Pro Ser Thr
    130                 135                 140

Glu Lys Met Tyr Val Glu Asp Gly Val Leu Lys Gly Asp Val Asn Met
145                 150                 155                 160

Arg Leu Leu Leu Glu Gly Gly Gly His Tyr Arg Cys Asp Phe Lys Thr
                165                 170                 175

Thr Tyr Lys Ala Lys Lys Glu Val Arg Leu Pro Asp Ala His Lys Ile
            180                 185                 190
```

```
Asp His Arg Ile Glu Ile Leu Lys His Asp Lys Asp Tyr Asn Lys Val
            195                 200                 205

Lys Leu Tyr Glu Asn Ala Val Ala Arg Tyr Ser Met Leu Pro Ser Gln
210                 215                 220

Ala Lys Gly Tyr Pro Ser His Trp Arg Pro Leu Glu
225                 230                 235

<210> SEQ ID NO 3
<211> LENGTH: 330
<212> TYPE: DNA
<213> ORGANISM: Homo sapiens

<400> SEQUENCE: 3
atgaatccca gtatgaagca gaaacaagaa gaaatcaaag agaatataaa gaatagttct      60
gtcccaagaa gaactctgaa gatgattcag ccttctgcat ctggatctct tgttggaaga    120
gaaaatgagc tgtccgcagg cttgtccaaa aggaaacatc ggaatgacca cttaacatct    180
acaacttcca gccctggggt tattgtccca gaatctagtg aaaataaaaa tcttggagga    240
gtcacccagg agtcatttga tcttatgatt aaagaaaatc catcctctca gtattggaag    300
gaagtggcag aaaaacggag aaaggcgctg                                      330

<210> SEQ ID NO 4
<211> LENGTH: 110
<212> TYPE: PRT
<213> ORGANISM: Homo sapiens

<400> SEQUENCE: 4

Met Asn Pro Ser Met Lys Gln Lys Gln Glu Glu Ile Lys Glu Asn Ile
1               5                   10                  15

Lys Asn Ser Ser Val Pro Arg Arg Thr Leu Lys Met Ile Gln Pro Ser
            20                  25                  30

Ala Ser Gly Ser Leu Val Gly Arg Glu Asn Glu Leu Ser Ala Gly Leu
        35                  40                  45

Ser Lys Arg Lys His Arg Asn Asp His Leu Thr Ser Thr Thr Ser Ser
    50                  55                  60

Pro Gly Val Ile Val Pro Glu Ser Ser Glu Asn Lys Asn Leu Gly Gly
65                  70                  75                  80

Val Thr Gln Glu Ser Phe Asp Leu Met Ile Lys Glu Asn Pro Ser Ser
                85                  90                  95

Gln Tyr Trp Lys Glu Val Ala Glu Lys Arg Arg Lys Ala Leu
            100                 105                 110

<210> SEQ ID NO 5
<211> LENGTH: 50
<212> TYPE: PRT
<213> ORGANISM: Artificial Sequence
<220> FEATURE:
<223> OTHER INFORMATION: VP64 peptide

<400> SEQUENCE: 5

Asp Ala Leu Asp Asp Phe Asp Leu Asp Met Leu Gly Ser Asp Ala Leu
1               5                   10                  15

Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Asp Phe Asp Leu Asp
        35                  40                  45

Met Leu
    50
```

-continued

<210> SEQ ID NO 6
<211> LENGTH: 396
<212> TYPE: PRT
<213> ORGANISM: Homo sapiens

<400> SEQUENCE: 6

Met Ala Phe Ala Pro Met Gly Pro Glu Ala Ser Phe Asp Val Leu
1               5                   10                  15

Asp Arg His Arg Glu Ser Leu Leu Ala Ala Leu Arg Arg Gly Gly Arg
            20                  25                  30

Glu Pro Pro Thr Gly Gly Ser Arg Leu Ala Ser Ser Glu Val Leu
            35                  40                  45

Ala Ser Ile Glu Asn Ile Ile Gln Asp Ile Ile Thr Ser Leu Ala Arg
    50                  55                  60

Asn Glu Ala Pro Ala Phe Thr Ile Asp Asn Arg Ser Ser Trp Glu Asn
65                  70                  75                  80

Ile Lys Phe Glu Asp Ser Val Gly Leu Gln Met Val Ser His Cys Thr
                85                  90                  95

Thr Arg Lys Ile Lys Ser Asp Ser Pro Lys Ser Ala Gln Lys Phe Ser
            100                 105                 110

Leu Ile Leu Lys Ile Leu Ser Met Ile Tyr Lys Leu Val Gln Ser Asn
        115                 120                 125

Thr Tyr Ala Thr Lys Arg Asp Ile Tyr Tyr Thr Asp Ser Gln Leu Phe
    130                 135                 140

Gly Asn Gln Thr Val Val Asp Asn Ile Ile Asn Asp Ile Ser Cys Met
145                 150                 155                 160

Leu Lys Val Ser Arg Arg Ser Leu His Ile Leu Ser Thr Ser Lys Gly
                165                 170                 175

Leu Ile Ala Gly Asn Leu Arg Tyr Ile Glu Glu Asp Gly Thr Lys Val
            180                 185                 190

Asn Cys Thr Cys Gly Ala Thr Ala Val Ala Val Pro Ser Asn Ile Gln
        195                 200                 205

Gly Ile Arg Asn Leu Val Thr Asp Ala Lys Phe Val Leu Ile Val Glu
    210                 215                 220

Lys Asp Ala Thr Phe Gln Arg Leu Leu Asp Asp Asn Phe Cys Asn Lys
225                 230                 235                 240

Leu Ser Pro Cys Ile Met Ile Thr Gly Lys Gly Val Pro Asp Leu Asn
                245                 250                 255

Thr Arg Leu Leu Val Lys Lys Leu Trp Asp Thr Phe His Val Pro Val
            260                 265                 270

Phe Thr Leu Val Asp Ala Asp Pro His Gly Ile Glu Ile Met Cys Ile
        275                 280                 285

Tyr Lys Tyr Gly Ser Met Ser Met Ser Phe Glu Ala His His Leu Thr
    290                 295                 300

Val Pro Ala Ile Arg Trp Leu Gly Leu Leu Pro Ser Asp Leu Lys Arg
305                 310                 315                 320

Leu Asn Val Pro Lys Asp Ser Leu Ile Pro Leu Thr Lys Arg Asp Gln
                325                 330                 335

Met Lys Leu Asp Ser Ile Leu Arg Arg Pro Tyr Val Thr Cys Gln Pro
            340                 345                 350

Phe Trp Arg Lys Glu Met Glu Ile Met Ala Asp Ser Lys Met Lys Ala
        355                 360                 365

```
Glu Ile Gln Ala Leu Thr Phe Leu Ser Ser Asp Tyr Leu Ser Arg Val
    370                 375                 380

Tyr Leu Pro Asn Lys Leu Lys Phe Gly Gly Trp Ile
385                 390                 395

<210> SEQ ID NO 7
<211> LENGTH: 358
<212> TYPE: PRT
<213> ORGANISM: Homo sapiens

<400> SEQUENCE: 7

Met Ala Phe Ala Pro Met Gly Pro Glu Ala Ser Phe Phe Asp Val Leu
1               5                   10                  15

Asp Arg His Arg Glu Ser Leu Ala Ala Leu Arg Arg Gly Gly Arg
            20                  25                  30

Glu Pro Pro Thr Gly Gly Ser Arg Leu Ala Ser Arg Phe Glu Asp Ser
            35                  40                  45

Val Gly Leu Gln Met Val Ser His Cys Thr Thr Arg Lys Ile Lys Ser
    50                  55                  60

Asp Ser Pro Lys Ser Ala Gln Lys Phe Ser Leu Ile Leu Lys Ile Leu
65                  70                  75                  80

Ser Met Ile Tyr Lys Leu Val Gln Ser Asn Thr Tyr Ala Thr Lys Arg
                85                  90                  95

Asp Ile Tyr Tyr Thr Asp Ser Gln Leu Phe Gly Asn Gln Thr Val Val
            100                 105                 110

Asp Asn Ile Ile Asn Asp Ile Ser Cys Met Leu Lys Val Ser Arg Arg
        115                 120                 125

Ser Leu His Ile Leu Ser Thr Ser Lys Gly Leu Ile Ala Gly Asn Leu
    130                 135                 140

Arg Tyr Ile Glu Glu Asp Gly Thr Lys Val Asn Cys Thr Cys Gly Ala
145                 150                 155                 160

Thr Ala Val Ala Val Pro Ser Asn Ile Gln Gly Ile Arg Asn Leu Val
                165                 170                 175

Thr Asp Ala Lys Phe Val Leu Ile Val Glu Lys Asp Ala Thr Phe Gln
            180                 185                 190

Arg Leu Leu Asp Asp Asn Phe Cys Asn Lys Leu Ser Pro Cys Ile Met
        195                 200                 205

Ile Thr Gly Lys Gly Val Pro Asp Leu Asn Thr Arg Leu Leu Val Lys
    210                 215                 220

Lys Leu Trp Asp Thr Phe His Val Pro Val Phe Thr Leu Val Asp Ala
225                 230                 235                 240

Asp Pro His Gly Ile Glu Ile Met Cys Ile Tyr Lys Tyr Gly Ser Met
                245                 250                 255

Ser Met Ser Phe Glu Ala His His Leu Thr Val Pro Ala Ile Arg Trp
            260                 265                 270

Leu Gly Leu Leu Pro Ser Asp Leu Lys Arg Leu Asn Val Pro Lys Asp
        275                 280                 285

Ser Leu Ile Pro Leu Thr Lys Arg Asp Gln Met Lys Leu Asp Ser Ile
    290                 295                 300

Leu Arg Arg Pro Tyr Val Thr Cys Gln Pro Phe Trp Arg Lys Glu Met
305                 310                 315                 320

Glu Ile Met Ala Asp Ser Lys Met Lys Ala Glu Ile Gln Ala Leu Thr
                325                 330                 335
```

```
Phe Leu Ser Ser Asp Tyr Leu Ser Arg Val Tyr Leu Pro Asn Lys Leu
            340                 345                 350
Lys Phe Gly Gly Trp Ile
        355

<210> SEQ ID NO 8
<211> LENGTH: 583
<212> TYPE: PRT
<213> ORGANISM: Flavobacterium okeanokoites

<400> SEQUENCE: 8

Met Phe Leu Ser Met Val Ser Lys Ile Arg Thr Phe Gly Trp Val Gln
1               5                   10                  15
Asn Pro Gly Lys Phe Glu Asn Leu Lys Arg Val Val Gln Val Phe Asp
                20                  25                  30
Arg Asn Ser Lys Val His Asn Glu Val Lys Asn Ile Lys Ile Pro Thr
            35                  40                  45
Leu Val Lys Glu Ser Lys Ile Gln Lys Glu Leu Val Ala Ile Met Asn
        50                  55                  60
Gln His Asp Leu Ile Tyr Thr Tyr Lys Glu Leu Val Gly Thr Gly Thr
65                  70                  75                  80
Ser Ile Arg Ser Glu Ala Pro Cys Asp Ala Ile Gln Ala Thr Ile
                85                  90                  95
Ala Asp Gln Gly Asn Lys Lys Gly Tyr Ile Asp Asn Trp Ser Ser Asp
                100                 105                 110
Gly Phe Leu Arg Trp Ala His Ala Leu Gly Phe Ile Glu Tyr Ile Asn
            115                 120                 125
Lys Ser Asp Ser Phe Val Ile Thr Asp Val Gly Leu Ala Tyr Ser Lys
        130                 135                 140
Ser Ala Asp Gly Ser Ala Ile Glu Lys Glu Ile Leu Ile Glu Ala Ile
145                 150                 155                 160
Ser Ser Tyr Pro Pro Ala Ile Arg Ile Leu Thr Leu Glu Asp Gly
                165                 170                 175
Gln His Leu Thr Lys Phe Asp Leu Gly Lys Asn Leu Gly Phe Ser Gly
                180                 185                 190
Glu Ser Gly Phe Thr Ser Leu Pro Glu Gly Ile Leu Leu Asp Thr Leu
            195                 200                 205
Ala Asn Ala Met Pro Lys Asp Lys Gly Glu Ile Arg Asn Asn Trp Glu
        210                 215                 220
Gly Ser Ser Asp Lys Tyr Ala Arg Met Ile Gly Gly Trp Leu Asp Lys
225                 230                 235                 240
Leu Gly Leu Val Lys Gln Gly Lys Lys Glu Phe Ile Ile Pro Thr Leu
                245                 250                 255
Gly Lys Pro Asp Asn Lys Glu Phe Ile Ser His Ala Phe Lys Ile Thr
                260                 265                 270
Gly Glu Gly Leu Lys Val Leu Arg Arg Ala Lys Gly Ser Thr Lys Phe
            275                 280                 285
Thr Arg Val Pro Lys Arg Val Tyr Trp Glu Met Leu Ala Thr Asn Leu
        290                 295                 300
Thr Asp Lys Glu Tyr Val Arg Thr Arg Arg Ala Leu Ile Leu Glu Ile
305                 310                 315                 320
Leu Ile Lys Ala Gly Ser Leu Lys Ile Glu Gln Ile Gln Asp Asn Leu
                325                 330                 335
Lys Lys Leu Gly Phe Asp Glu Val Ile Glu Thr Ile Glu Asn Asp Ile
                340                 345                 350
```

```
Lys Gly Leu Ile Asn Thr Gly Ile Phe Ile Glu Ile Lys Gly Arg Phe
                355                 360                 365

Tyr Gln Leu Lys Asp His Ile Leu Gln Phe Val Ile Pro Asn Arg Gly
            370                 375                 380

Val Thr Lys Gln Leu Val Lys Ser Glu Leu Glu Glu Lys Lys Ser Glu
385                 390                 395                 400

Leu Arg His Lys Leu Lys Tyr Val Pro His Glu Tyr Ile Glu Leu Ile
                405                 410                 415

Glu Ile Ala Arg Asn Ser Thr Gln Asp Arg Ile Leu Glu Met Lys Val
            420                 425                 430

Met Glu Phe Phe Met Lys Val Tyr Gly Tyr Arg Gly Lys His Leu Gly
                435                 440                 445

Gly Ser Arg Lys Pro Asp Gly Ala Ile Tyr Thr Val Gly Ser Pro Ile
            450                 455                 460

Asp Tyr Gly Val Ile Val Asp Thr Lys Ala Tyr Ser Gly Gly Tyr Asn
465                 470                 475                 480

Leu Pro Ile Gly Gln Ala Asp Glu Met Gln Arg Tyr Val Glu Glu Asn
                485                 490                 495

Gln Thr Arg Asn Lys His Ile Asn Pro Asn Glu Trp Trp Lys Val Tyr
            500                 505                 510

Pro Ser Ser Val Thr Glu Phe Lys Phe Leu Phe Val Ser Gly His Phe
                515                 520                 525

Lys Gly Asn Tyr Lys Ala Gln Leu Thr Arg Leu Asn His Ile Thr Asn
            530                 535                 540

Cys Asn Gly Ala Val Leu Ser Val Glu Glu Leu Leu Ile Gly Gly Glu
545                 550                 555                 560

Met Ile Lys Ala Gly Thr Leu Thr Leu Glu Glu Val Arg Arg Lys Phe
                565                 570                 575

Asn Asn Gly Glu Ile Asn Phe
            580

<210> SEQ ID NO 9
<211> LENGTH: 1752
<212> TYPE: DNA
<213> ORGANISM: Flavobacterium okeanokoites

<400> SEQUENCE: 9 atgttttga gtatggtttc taaaataaga actttcggtt gggttcaaaa tccaggtaaa       60
tttgagaatt taaaacgagt agttcaagta tttgatagaa attctaaagt acataatgaa      120
gtgaaaaata taaagatacc aaccctagtc aaagaaagta agatccaaaa agaactagtt      180
gctattatga atcaacatga tttgatttat acatataaag agttagtagg aacaggaact      240
tcaatacgtt cagaagcacc atgcgatgca attattcaag caacaatagc agatcaagga      300
aataaaaaag gctatatcga taattggtca tctgacggtt ttttgcgttg ggcacatgct      360
ttaggattta ttgaatatat aaataaaagt gattcttttg taataactga tgttggactt      420
gcttactcta aatcagctga cggcagcgcc attgaaaaag gatttttgat gaagcgata      480 tcatcttatc ctccagcgat tcgtatttta actttgctag aagatggaca acatttgaca      540
aagtttgatc ttggcaagaa tttaggtttt agtggagaaa gtggatttac ttctctaccg      600
gaaggaattc ttttagatac tctagctaat gctatgccta agataaagg cgaaattcgt      660 aataattggg aaggatcttc agataagtac gcaagaatga taggtggttg gctggataaa      720
ctaggattag taaagcaagg aaaaaaagaa tttatcattc ctactttggg taagccggac      780
```

```
aataaagagt ttatatccca cgcttttaaa attactggag aaggtttgaa agtactgcgt      840
cgagcaaaag gctctacaaa atttacacgt gtacctaaaa gagtatattg ggaaatgctt      900
gctacaaacc taaccgataa agagtatgta agaacaagaa gagctttgat tttagaaata     960
ttaatcaaag ctggatcatt aaaaatagaa caaatacaag acaacttgaa gaaattagga    1020
tttgatgaag ttatagaaac tattgaaaat gatatcaaag gcttaattaa cacaggtata    1080
tttatagaaa tcaaagggcg attttatcaa ttgaaagacc atattcttca atttgtaata    1140
cctaatcgtg gtgtgactaa gcaactagtc aaaagtgaac tggaggagaa gaaatctgaa    1200
cttcgtcata aattgaaata tgtgcctcat gaatatattg aattaattga aattgccaga    1260
aattccactc aggatagaat tcttgaaatg aaggtaatgg aatttttat gaaagtttat     1320 ggatatagag gtaaacattt gggtggatca aggaaaccgg acggagcaat ttatactgtc    1380
ggatctccta ttgattacgg tgtgatcgtg gatactaaag cttatagcgg aggttataat    1440
ctgccaattg gccaagcaga tgaaatgcaa cgatatgtcg aagaaaatca aacacgaaac    1500
aaacatatca accctaatga atggtggaaa gtctatccat cttctgtaac ggaatttaag    1560 ttttatttg tgagtggtca ctttaaagga aactacaaag ctcagcttac acgattaaat    1620
catatcacta attgtaatgg agctgttctt agtgtagaag agcttttaat tggtggagaa    1680
atgattaaag ccggcacatt aaccttagag gaagtgagac ggaaatttaa taacggcgag    1740
ataaactttt aa                                                         1752
```

METHODS FOR INCREASING EFFICIENCY OF NUCLEASE-INDUCED HOMOLOGY-DIRECTED REPAIR

CLAIM OF PRIORITY

This application is a U.S. National Phase Application under 35 U.S.C. § 371 of International Patent Application No. PCT/US2015/053417, filed on Oct. 1, 2015, which claims the benefit of U.S. Provisional Patent Application Ser. No. 62/058,456, filed on Oct. 1, 2014. The entire contents of the foregoing are hereby incorporated by reference.

TECHNICAL FIELD

The present invention relates to methods to improve the absolute rate of homology-directed repair (HDR) and/or to improve the relative rate of HDR compared with non-homologous end joining (NHEJ).

BACKGROUND

Targeted genome editing is an emerging and important technology with broad research and therapeutic applications. Customizable nucleases can be used to make targeted double-stranded breaks (DSB) in living cells, the repair of which can be exploited to induce desired sequence changes.

Two competing pathways effect repairs in most cells, including mammalian cells. Repair of a nuclease-induced DSB by non-homologous end joining (NHEJ) leads to the introduction of insertion/deletion mutations (indels) with high frequencies. By contrast, DSB repair by homology directed repair (HDR) with a user-supplied "donor template" DNA can lead to the introduction of specific alterations (e.g., point mutations and insertions) or the correction of mutant sequences back to wild-type.

SUMMARY

The present invention is based on the development of methods for improving the absolute rate of homology-directed repair (HDR) and/or the relative rate of HDR compared with non-homologous end joining (NHEJ).

Thus, in one aspect, the invention provides methods for introducing a specific sequence into a target site on a double-stranded nucleic acid in a cell, e.g., genomic DNA. The methods include contacting the cell with or expressing in the cell (i) a double-stranded region of a donor nucleic acid molecule comprising the specific sequence to be inserted into the target nucleic acid and (ii) a DNA binding domain (DBD), e.g., an engineered DNA binding domain, that binds to or near (e.g., within 50, 30, 20, 10, or 5 nucleotides of) the target site, wherein the DBD also binds to a double-stranded region of a donor nucleic acid molecule comprising the specific sequence to be inserted into the target nucleic acid; and inducing a double stranded break (DSB) at the target site, under conditions sufficient for the donor nucleic acid molecule to be inserted into the site of the DSB and the DSB to be repaired, thereby introducing the specific sequence into the target site.

In some embodiments, the DBD is a zinc finger domain, a transcription-activator-like effector (TALE) domain, or a "dead" Cas9 variant lacking nucleases activity ("dCas9"), that binds directly to a double-stranded DNA portion of the donor molecule that is near (e.g., within 50, 30, 20, 10, or 5 nucleotides of) the target site.

In some embodiments, the nuclease is ZFN, TALEN, or Cas9 protein.

In some embodiments, the methods include expressing a fusion protein comprising a DBD linked, e.g., via an optional intervening linker of from 1-100, 1-50, 1-30, or 1-20 amino acids, to the nuclease used to make the DSB.

In some embodiments, the DBD is linked to a second DBD that binds adjacent to or near, e.g., within 50, 30, 20, or 10 nts of, the target DSB site.

In some embodiments, the donor molecule is wholly double-stranded donor template or partially double-stranded and partially single-stranded DNA.

In some embodiments, the methods include expressing in the cell: a first fusion protein comprising a dimerization domain and the DBD that binds to a donor nucleic acid molecule (rather than covalent linkages), and a second fusion protein comprising a corresponding dimerization domain and a nuclease that induces a DSB at the target site or a second DBD that binds a DNA sequence adjacent to the target DSB.

In some embodiments, the DBD that binds the donor molecule is fused or bound to Csy4, the nuclease is Cas9, and the guideRNA is fused to a Csy4 recognition sequence.

In some embodiments, the nuclease is fused to a catalytically inactive Csy4 (dCsy4), and the donor molecule is a RNA-DNA hybrid comprising a Csy4 recognition site (RNA) and a double-stranded donor (DNA).

In another aspect, the invention provides methods for introducing a specific sequence into a target site on a double-stranded nucleic acid in a cell, e.g., genomic DNA. The methods include expressing in the cell a nuclease that induces DSBs only in specific phases of the cell cycle, comprising a fusion protein comprising a cell-cycle regulated protein domain linked to an engineered nucleases.

In some embodiments, the cell-cycle regulated protein domain is from a G2 or S-phase specific proteins, e.g., CtIP, Cdk2, Cyclin A1, Cyclin A2, Cyclin B1, or Gemini, e.g., amino acids 1-100 of human Gemini.

In some embodiments, the engineered nuclease is selected from the group consisting of a ZFN, a TALEN, a CRISPR/Cas9, and a CRISPR RNA-guided FokI nucleases (RFNs).

In some embodiments, the fusion protein is selected from the group consisting of hGem-ZFN, ZFN-hGem, mAG-hGem-ZFN, ZFN-mAG-hGem, hGem-TALEN, TALEN-hGem, mAG-hGem-TALEN, TALEN-mAG-hGem; hGem-Cas9, Cas9-hGem, mAG-hGem-Cas9, Cas9-mAG-hGem, hGem-Csy4, hGem-mAG-Csy4, Csy4-hGem, or Csy4-mAG-hGem, hGem-FokI-dCas9, hGem-mAG-FokI-dCas9, FokI-dCas9-hGem, FokI-dCas9-hGem-mAG, hGem-dCas9-FokI, hGem-mAG-dCas9-FokI, dCas9-FokI-hGem, or dCas9-FokI-hGem-mAG.

In some embodiments, the constructs comprise one or more nuclear localization signals and nuclear export signals, or nuclear-cytoplasmic shuttle sequences to control the trafficking of nuclease proteins into the cytoplasm.

In another aspect, the invention provides methods for introducing a specific sequence into a target site on a double-stranded nucleic acid in a cell, e.g., genomic DNA, the method comprising globally expressing one or more components of the HDR pathway throughout the cell cycle.

In some embodiments, the methods include contacting the cell with or expressing in the cell an engineered fusion protein comprising a transcriptional activation domains (e.g., VP64, VP16, NF-KB p65) and a sequence-specific DNA binding domains (e.g., engineered zinc fingers, TALEs, or dCas9 complexed with specific guide RNAs), to thereby upregulate a components of the HDR pathway.

In some embodiments, the factors to upregulate include one or more of Rad50, Rad51, Rad52, Rad54, BRCA1, or BRCA2.

In another aspect, the invention provides methods for introducing a specific sequence into a target site on a double-stranded nucleic acid in a cell, e.g., genomic DNA. The methods include expressing in the cell an engineered nuclease (e.g., ZFN, TALEN, Cas9 nuclease, Cas9 nickase, or CRISPR RNA-guided FokI nuclease) to generate a DSB at the target site, and recruiting HDR factors to or blocking NHEJ factors from the same genomic site.

In some embodiments, the methods include expressing in the cell one or more of: a fusion protein comprising an HDR factor linked to a DBD that binds to a sequence near the target site, a fusion protein comprising an HDR factor linked to the engineered nuclease, a first fusion protein comprising an HDR factor linked to a dimerization domain and a second fusion protein comprising an engineered nuclease linked to a corresponding dimerization domain, a fusion protein comprising an HDR factor linked to an RNA-binding protein (e.g., MS2 or Csy4) that interacts with a specific RNA sequence appended to the end of a guide RNA sequence, and/or expression from a plasmid of any pro-HDR or anti-NHEJ factor.

In some embodiments, the HDR factor is selected from the group consisting of nucleases or helicases to process free DNA ends, and protein binding domains to act as nucleation sites for supplementary HDR factors.

In some embodiments, the HDR-related protein is selected from the group consisting of Nucleases and/or helicases that promote DNA strand resection, e.g., MRE11, EXO1, DNA2, CtIP, TREX2, and Apollo; Binding factors/nucleation proteins that recruit specific factors or catalyze strand invasion, e.g., BRCA1, BRCA2, PALB2, RAD50 or NBS1, RAD51, RAD52, RAD54, SRCAP, FANCI, FANCD2, BRIP1, SLX4, FANCA, FANCE, and FANCL (including truncated, mutated, modified, or optimized versions of these factors).

In another aspect, the invention provides methods for introducing a specific sequence into a target site on a double-stranded nucleic acid in a cell, e.g., genomic DNA. The methods include locally blocking or binding NHEJ-associated factors, including transcriptional repression of pro-NHEJ factors.

In some embodiments, the methods include expressing in the cell a fusion protein comprising a DBD that binds to or near the target site fused to a version of DNA-PK that interact and bind Ku70 but is impaired for recruitment of end-processing factors such as Artemis, polynucleotide kinase/phosphatase (PNKP), AP endonuclease 1 (APE1) and tyrosyl-DNA posphodiesterase (TDP1), or fused to a defective version of Rif1.

In another aspect, the invention provides methods for introducing a specific sequence into a target site on a double-stranded nucleic acid in a cell, e.g., genomic DNA. The methods include inducing a double stranded break (DSB) at the target site, wherein the DSB has 3' overhangs.

In some embodiments, the methods include expressing in the cell: pairs of engineered nickases (e.g., ZFNickases or Cas9 nickases) positioned to form a DSB with 3' overhangs; one or more ZFN, TALEN, or CRISPR RNA-guided nucleases comprising dimerization-dependent nuclease domains that make DSBs with 3' overhangs, e.g., a nuclease domain from Kpn I; or a fusion protein comprising a FokI cleavage domain fused to a Cas9 nickase (e.g., H840- or N863A-Cas9 nickase), and two guide RNAs spaced to generate a DSB with 3' overhangs.

In another aspect, the invention provides methods for introducing a specific sequence into a target site on a double-stranded nucleic acid in a cell, e.g., genomic DNA. The methods include expressing in the cell a pair of fusion proteins, each comprising an engineered DNA binding domain linked to Spo11 (in either N-, C-, or internal fusions), wherein each of the DBD-Spo11 monomer is targeted with appropriate spacing to create targeted DSBs with 3' overhangs.

In another aspect, the invention provides methods for introducing a specific sequence into a target site on a double-stranded nucleic acid in a cell, e.g., genomic DNA. The methods include expressing in a cell a fusion protein comprising Cas9 and a chromatin modifier, e.g., SETD2, SRCAP, and SMARCAD1.

In another aspect, the invention provides methods for introducing a specific sequence into a target site on a double-stranded nucleic acid in a cell, e.g., genomic DNA, by use of an in vitro produced protein-capped donor template.

In some embodiments, the methods include expressing a Cas9-based nuclease or nickase, further comprising expressing in the cell one or more guide RNAs that bind to or near the target site.

In some embodiments, the absolute rate of homology-directed repair (HDR) and/or the relative rate of HDR as compared with the rate of non-homologous end joining (NHEJ) is improved.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 3A-D show exemplary schematics for fusing HDR-factors to Cas9. (a) Cas9 nuclease or nickase shown in yellow with N- and C-terminal ends highlighted, and the guide-RNA shown in red (b) full length or truncated domain versions of HDR-effector molecules can be fused to either or both of the N- or C-terminal ends of Cas9 variants. (c) HDR-effectors can be recruited to Cas9 through the use of dimerization domains. (d) When fused to RNA-binding proteins, HDR-effectors can be recruited to the Cas9/gRNA complex if an RNA-binding motif is appended to the 3'-end of the gRNA.

FIG. 4 is a schematic illustrating exemplary paired Cas9 nickases (Cas9n) for formation of DSBs with 3' overhangs.

FIG. 5 is a schematic illustrating exemplary FokI-Cas9 nickase (Cas9n) architecture for introducing 3' overhangs.

DETAILED DESCRIPTION

A major unresolved challenge for genome editing is the inability to control whether a DSB is repaired by HDR with the donor template or by mutagenic NHEJ. HDR-mediated alterations can potentially be used to achieve the precise genome editing events that will be required for therapeutic applications, but the efficiencies with which these alterations are generally less efficient than NHEJ-mediated indels. Because alteration by HDR and NHEJ are competitive processes, indels can be introduced before desired precise changes. In addition, in some cases, secondary NHEJ-mediated indels can be introduced into alleles that have been corrected by HDR.

A method that would enable HDR to become more efficient than NHEJ or a method that suppressed NHEJ-mediated repair would broaden the scope of applications for nuclease-induced genome editing. Here we describe a number of strategies for increasing the absolute and relative rates of HDR by customizable nucleases. Note that although we describe these strategies using the clustered regularly interspaced short palindromic repeat-CRISPR-associated (CRISPR-Cas9) system to induce DSBs, many of these strategies are generalizable for use with any customizable nuclease platform (e.g.—meganucleases, zinc finger nucleases (ZFNs), transcription activator-like effector nucleases (TALENs)).

Method #1: Increasing HDR by Increasing the Local Concentration of Donor Molecule, by Tethering a Donor Template Near the Site of a Nuclease-Induced DSB A first method to enhance HDR by targeted DNA cleavage is to use an engineered DNA binding domain to physically localize the HDR donor molecule to the site of the targeted DSB. The rationale for this approach is that increasing the local concentration of donor molecule around a DSB will drive the subsequent DNA repair reaction toward targeted HDR-mediated repair (because a homologous donor molecule is required for the reaction to proceed), where the desired reaction is:

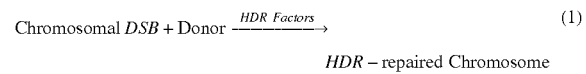
(1)

and the competing NHEJ-mediated repair reaction is given by:

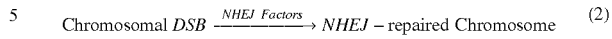
(2)

such that the velocity of reaction (1) will increase as a result of the increased concentration of donor, while reaction (2) will not be directly affected by this perturbation; however, a bias toward reaction (1) could cause reaction (2) to proceed less efficiently.

Figure 1A:
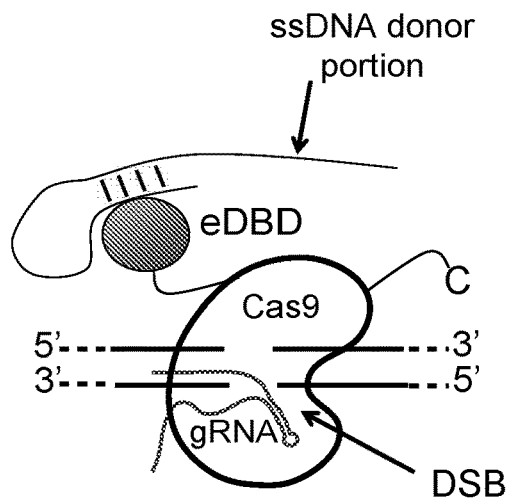
FIG. 1 is a Schematic for donor recruitment to nuclease induced DSB. Reflective of the many combinatorial variations possible in this system, only a few possible configurations are shown. In each case, the dsDNA binding site is highlighted in green. Regions of double-stranded DNA are represented by dashes between two strands. (a-b) Direct fusion of donor-recruiting DNA-binding domains (DBDs) to the N-terminus of Cas9, where the configuration in (a) relies on binding to a dsDNA portion of an otherwise ssDNA donor molecule, while that in (b) binds to a dsDNA portion of a molecule that partially hybridizes with the ssDNA donor molecule. (c) C-terminal fusion of Cas9 to a dimerization domain whose binding partner is fused to a DBD targeted to a sequence in a dsDNA donor plasmid.
Figure 1B:
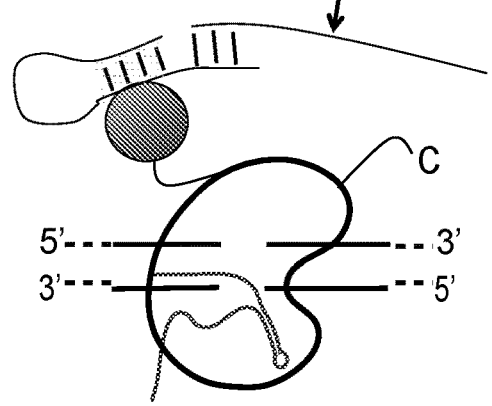

This can be achieved using a DNA binding domain (DBD), e.g., an engineered DNA binding domain with programmable specificity, such as a zinc finger domain, a transcription-activator-like effector (TALE) domain, a "dead" Cas9 variant lacking nucleases activity ("dCas9"), or other DNA-binding platforms, e.g., as described herein—that binds directly to a double-stranded DNA portion of the donor molecule and localizes it to the site of the DSB. This DBD directs DSB localization in the target DNA, e.g., in the genome, through direct fusion to a nuclease used to make the DSB (such as a ZFN, TALEN, or Cas9 protein; see, for example, FIGS. 1a & 1b) or through fusion to a second engineered DNA binding domain (of the same or a different type) that has been engineered to bind to a sequence near the target DSB site in the target DNA, e.g., in the genome. In either case, the first DBD can bind to either a wholly double-stranded donor template, to a double-stranded portion of an otherwise single-stranded DNA donor molecule, or to a double-stranded portion of a DNA molecule whose single-strand portion hybridizes to a single-stranded portion of a donor molecule.

Figure 1C:
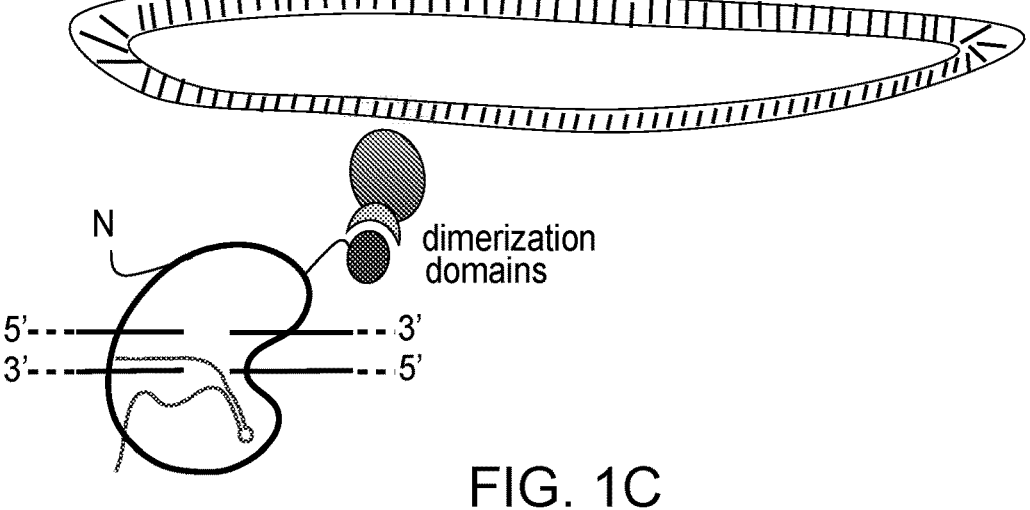
Figure 2A:
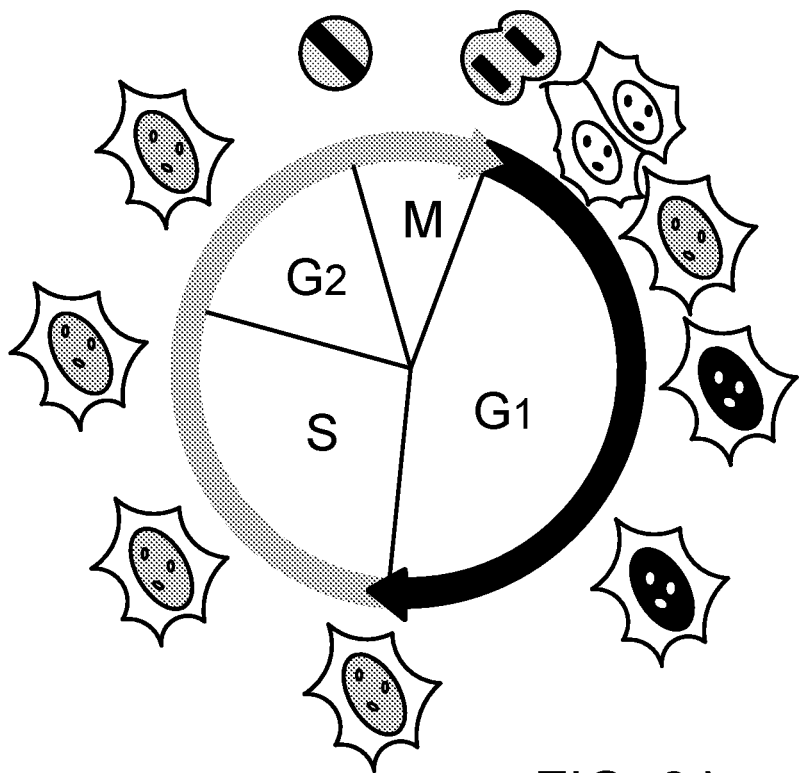
FIGS. 2A-B illustrate cell-cycle localized fluorescent markers. (a) Schematic adapted from Miyawaki et al. 2008. The cell-cycle tagged fluorescent proteins described in this work are mAzamiGreen-hGem (localized to S/G2/M) and mKusabiraOrange2-Cdt1 (localized to G1). (b) Confocal imaging of a cell line the present inventors established that expresses both of these cell-cycle indicators.
Figure 2B:
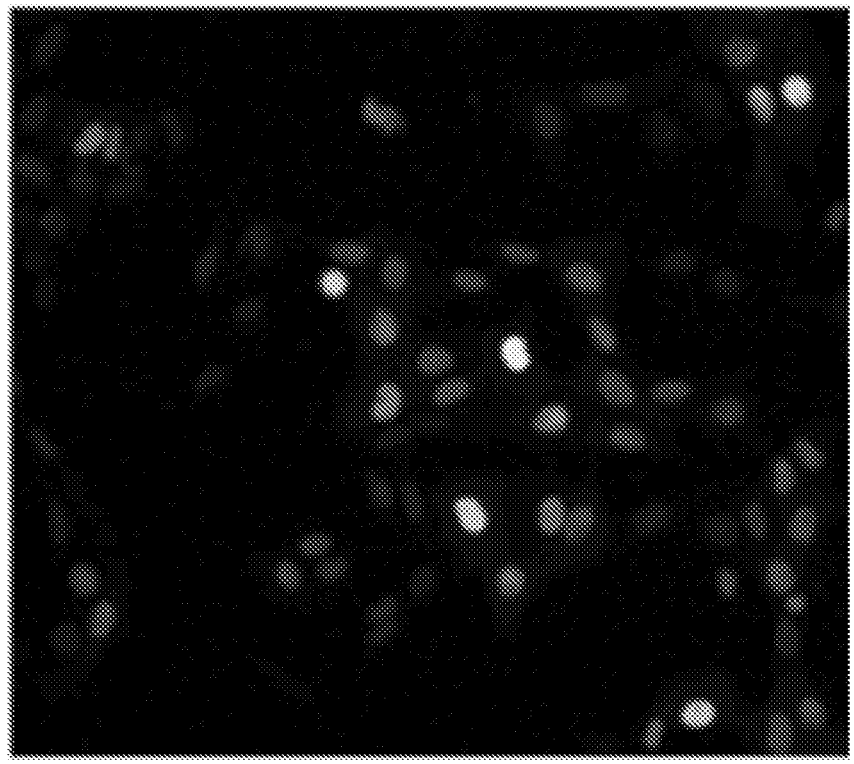

Other variations on this approach include the use of dimerization domains (rather than covalent linkages) to join together the DBD that binds to or recruits the donor molecule with either the DSB-inducing nuclease(s) or a second DBD that binds DNA sequence adjacent to the target DSB (FIG. 1c). These dimerization domains might constitutively interact with one another (e.g., leucine zipper motifs (Feuerstein et al., Proc. Nati. Acad. Sci. USA 91:10655-10659, 1994), Fc domains) or might interact only in the presence of an effector such as a small molecule or stimulation by light. A number of dimerization domains are known in the art, e.g., cysteines that are capable of forming an intermolecular disulfide bond with a cysteine on the partner fusion protein, a coiled-coil domain, an acid patch, a zinc finger domain, a calcium hand domain, a CHI region, a CL region, a leucine zipper domain, an SH2 (src homology 2) domain, an SH3 (src Homology 3) domain, a PTB (phosphotyrosine binding) domain, a WW domain, a PDZ domain, a 14-3-3 domain, a WD40 domain, an EH domain, a Lim domain, an isoleucine zipper domain, and a dimerization domain of a receptor dimer pair (see, e.g., US20140170141; US20130259806; US20130253040; and US20120178647). Suitable dimerization domains can be selected from any protein that is known to exist as a multimer or dimer, or any protein known to possess such multimerization or dimerization activity. Examples of suitable domains include the dimerization element of Gal4, leucine zipper domains, STAT protein N-terminal domains, FK506 binding proteins, and randomized peptides selected for Zf dimerization activity (see, e.g., Bryan et al., 1999, Proc. Natl. Acad. Sci. USA, 96:9568; Pomerantz et al., 1998, Biochemistry, 37:965-970; Wolfe et al., 2000, Structure, 8: 739-750; O'Shea, 1991, Science, 254:539; Barahmand-Pour et al., 1996, Curr. Top. Microbiol. Immunol., 211:121-128; Klemm et al., 1998, Annu Rev. Immunol., 16:569-592; Ho et al., 1996, Nature, 382: 822-826). Furthermore, some zinc finger proteins themselves have dimerization activity. For example, the zinc fingers from the transcription factor Ikaros have dimerization activity (McCarty et al., 2003, Mol. Cell, 11:459-470). Thus, if the engineered Zf proteins themselves have dimerization function there will be no need to fuse an additional dimerization domain to these proteins. In some embodiments the endonuclease domain itself possesses dimerization activity. For example, the nuclease domain of Fok I, which has intrinsic dimerization activity, can be used (Kim et al., 1996, Proc. Natl. Acad. Sci., 93:1156-60). In some embodiments, "conditional" dimerization technology can be used. For example, this can be accomplished using FK506 and FKBP interactions. FK506 binding domains are attached to the proteins to be dimerized. These proteins will remain separate in the absence of a dimerizer. Upon addition of a dimerizer, such as the synthetic ligand FK1012, the two proteins will fuse.

Alternatively, the DBD that binds the donor molecule might be recruited to the DSB through fusion or non-covalent interaction with a factor that directly binds an RNA sequence or structure (e.g., an "RNA aptamer") appended to the Cas9 guide RNA (gRNA); for example, Csy4 can bind to a Csy4 recognition sequence that is fused to the gRNA.

Another variation on this approach would be to fuse a nuclease (such as a ZFN, TALEN, Cas9, or FokI-dCas9) to a RNA-binding domain such as catalytically inactive Csy4 (dCsy4, e.g., H29A Csy4 as described in Haurwitz et al., EMBO J. Jun. 13, 2012; 31(12): 2824-2832; Lee et al., Proc Natl Acad Sci USA. Apr. 2, 2013; 110(14): 5416-5421) and provide a RNA-DNA hybrid donor molecule consisting of Csy4 recognition site (RNA) and a standard donor (DNA). dCsy4 will bind to a Csy4 recognition site on the single stranded RNA-DNA hybrid donor and tether it in close local proximity to the targeted DSB. Alternatively, an RNA-binding domain such as MS2 could be used in place of Csy4. Notably, Cas9 has been previously reported to remain bound after cleavage, which makes it ideal for this application.

We note that, in some cases, non-programmable natural DNA domains might also be used in lieu of engineered DBDs to achieve similar ends to those described above.

Method #2: Use of Cell-Cycle Regulated Nucleases

NHEJ operates during all phases of the cell cycle, while HDR is restricted to the S and G2 phases of the cell cycle.

HDR machinery is regulated during the cell cycle and is present during S and G2 phases. DSBs created during M or G1 phases are preferentially repaired by NHEJ, while those made during S and G2 have the opportunity to be repaired by HDR. The expression of many endogenous cellular proteins are regulated in a cell-cycle specific manner by ubiquitination or phosphorylation-dependent degradation mechanisms. For example, the Geminin protein is degraded during the G1 phase of the cell cycle, but accumulates during S, G2, and M phases. Fusions of a fluorescent protein monomeric Azami Green (mAG) to portions of human Geminin (hGem) have been demonstrated to restrict fluorescence activity to S, G2, and M phases of the cell cycle; see, e.g., Sakaue-Sawano et al., Cell. (2008) 132:487-98; Abe et al., Development 140, 237-246 (2013); Sakaue-Sawano et al., BMC Cell Biol. 12:2 (2011); and US20100100977.

mAG Nucleotide Sequence:

(SEQ ID NO: 1)
ATGGTGAGCGTGATCAAGCCCGAGATGAAGATCAAGCTGTGCATGAGGG

GCACCGTGAACGGCCACAACTTCGTGATCGAGGGCGAGGGCAAGGGCAA

CCCCTACGAGGGCACCCAGATCCTGGACCTGAACGTGACCGAGGGCGCCC

CCCTGCCCTTCGCCTACGACATCCTGACCACCGTGTTCCAGTACGGCAAC

AGGGCCTTCACCAAGTACCCCGCCGACATCCAGGACTACTTCAAGCAGAC

CTTCCCCGAGGGCTACCACTGGGAGAGGAGCATGACCTACGAGGACCAGG

GCATCTGCACCGCCACCAGCAACATCAGCATGAGGGGCGACTGCTTCTTC

TACGACATCAGGTTCGACGGCACCAACTTCCCCCCCAACGGCCCCGTGAT

GCAGAAGAAGACCCTGAAGTGGGAGCCCAGCACCGAGAAGATGTACGTG

GAGGACGGCGTGCTGAAGGGCGACGTGAACATGAGGCTGCTGCTGGAGG

GCGGCGGCCACTACAGGTGCGACTTCAAGACCACCTACAAGGCCAAGAA

GGAGGTGAGGCTGCCCGACGCCCACAAGATCGACCACAGGATCGAGATC

CTGAAGCACGACAAGGACTACAACAAGGTGAAGCTGTACGAGAACGCCG

TGGCCAGGTACTCCATGCTGCCCAGCCAGGCCAAGGGATATCCATCACAC

TGGCGGCCGCTCGAG mAG Amino Acid Sequence:

(SEQ ID NO: 2)
MVSVIKPEMKIKLCMRGTVNGHNFVIEGEGKGNPYEGTQILDLNVTEGAP

LPFAYDILTTVFQYGNRAFTKYPADIQDYFKQTFPEGYHWERSMTYEDQG

ICTATSNISMRGDCFFYDIRFDGTNFPPNGPVMQKKTLKWEPSTEKMYVE

DGVLKGDVNMRLLLEGGGHYRCDFKTTYKAKKEVRLPDAHKIDHRIEILK

HDKDYNKVKLYENAVARYSMLPSQAKGYPSHWRPLE hGem Nucleotide Sequence:

(SEQ ID NO: 3)
ATGAATCCCAGTATGAAGCAGAAACAAGAAGAAATCAAAGAGAATATAA

AGAATAGTTCTGTCCCAAGAAGAACTCTGAAGATGATTCAGCCTTCTGCA

TCTGGATCTCTTGTTGGAAGAGAAAATGAGCTGTCCGCAGGCTTGTCCAA

AAGGAAACATCGGAATGACCACTTAACATCTACAACTTCCAGCCCTGGGG

TTATTGTCCCAGAATCTAGTGAAAATAAAAATCTTGGAGGAGTCACCCAG

GAGTCATTTGATCTTATGATTAAAGAAAATCCATCCTCTCAGTATTGGAA

GGAAGTGGCAGAAAAACGGAGAAAGGCGCTG hGem Amino Acid Sequence:

(SEQ ID NO: 4)
MNPSMKQKQEEIKENIKNSSVPRRTLKMIQPSASGSLVGRENELSAGLSK
RKHRNDHLTSTTSSPGVIVPESSENKNLGGVTQESFDLMIKENPSSQYWK
EVAEKRRKAL

Here we describe methods to enhance HDR over NHEJ by the use of nucleases that induce DSBs only in specific phases of the cell cycle, that use fusions of cell-cycle regulated protein domains (e.g., hGEM, or amino acids 1-110 of hGEM) to engineered nucleases, such as ZFNs, TALENs, CRISPR/Cas9, and FokI-dCas9 or the Csy4 ribonuclease.

For ZFNs, in some embodiments exemplary fusion proteins would include hGem-ZFN, ZFN-hGem, mAG-hGem-ZFN, or ZFN-mAG-hGem.

For TALENs, in some embodiments exemplary fusion proteins would include hGem-TALEN, TALEN-hGem, mAG-hGem-TALEN, or TALEN-mAG-hGem.

For the wildtype CRISPR/Cas9 there are two components that can be regulated: Cas9 protein and the gRNA. First, exemplary Cas9 fusion proteins include hGem-Cas9, Cas9-hGem, mAG-hGem-Cas9, or Cas9-mAG-hGem. Second, activity of the gRNAs can be regulated by flanking with Csy4-recognition sites and placing it under control of a RNA Pol II promoter. In this context (see U.S. Ser. No. 61/930, 782), Cas9/gRNA activity depends on co-expression of and processing by the Csy4 ribonuclease. Placing Csy4 under cell cycle control (hGem-Csy4, hGem-mAG-Csy4, Csy4-hGem, or Csy4-mAG-hGem) is a potential strategy for regulating the activity of gRNAs by regulating the expression of Csy4.

For CRISPR RNA-guided FokI nucleases (RFNs), embodiments include hGem-FokI-dCas9, hGem-mAG-FokI-dCas9, FokI-dCas9-hGem, FokI-dCas9-hGem-mAG, hGem-dCas9-FokI, hGem-mAG-dCas9-FokI, dCas9-FokI-hGem, or dCas9-FokI-hGem-mAG.

Each of these constructs could additionally have combinations of nuclear localization signals and nuclear export signals, or nuclear-cytoplasmic shuttle sequences to control the trafficking of nuclease proteins into the cytoplasm, a critical step for ubiquitination and subsequent protein degradation. A PEST protein degradation tag, which is a peptide sequence that is rich in proline (P), glutamic acid (E), serine (S), and threonine (T) (see, e.g., Rogers et al., Science 234 (4774): 364-8 (1986)) could be added to generally reduce the half-life of the protein.

Instead of hGem, cell-cycle regulatory domains from other G2 or S-phase specific proteins could also be used, including but not limited to: CtIP, Cdk2, Cyclin A1, Cyclin A2, and Cyclin B1. Preferably, human sequences would be used.

Additionally, cell-cycle-specific regulation could be achieved by expressing a nuclease such as Cas9, TALENs, or engineered zinc finger nucleases under the control of cell-cycle-specific transcription regulatory elements. Promoters or regulatory elements of genes controlled by the transcription factor E2F, such as Cyclin-A, Cyclin-E, and CDC2, could be used to express the nuclease during S phase only. The SV40 promoter has also been demonstrated to express primarily during S phase.

Individually, or in combination, these methods may restrict expression of the desired nuclease to the S and G2 phases of the cell cycle, thereby increasing the probability that the induced DSB is repaired by the HDR pathway.

Method #3: Activation of Critical Endogenous Gene Products for HDR

Protein factors involved in the HDR pathway are regulated in a cell cycle-dependent manner. This restricts DSB repair by the HDR pathway to the S and G2 phases of the cell cycle, making precise alterations introduced by HDR inefficient relative to the indel-inducing NHEJ pathway. A strategy for more efficiently using HDR to make precise alterations to the genome is to globally express the critical components of the HDR pathway throughout the cell cycle. Specific methods for accomplishing this include using engineered fusions of transcriptional activation domains (e.g., VP64, VP16, NF-KB p65) to sequence-specific DNA binding domains (engineered zinc fingers, TALEs, or dCas9 complexed with specific guide RNAs) to upregulate critical components of the HDR pathway. Transcription activators that can be used in the TALE activators are known in the art, e.g., one or more, preferably four, VP16 peptides (e.g., the VP64 transcriptional activator sequence DALDDFDLDMLGSDALDDFDLDMLGS-DALDDFDLDMLGSDALDDFDLDML (SEQ ID NO:5), or an NF-KB p65 transactivation domain. See, e.g., Tremblay et al., Hum Gene Ther. 2012 August; 23(8):883-90; Li et al., Scientific Reports 2:897 (2012) DOI: 10.1038/srep00897; Maeder et al., Nat Methods. 2013 March; 10(3): 243-5; and US 20110301073.

Factors that can be up-regulated include but are not limited to: Rad50, Rad51, Rad52, Rad54, BRCA1, BRCA2, and Apollo. Each of these factors can be upregulated alone or in any combination of the factors listed. For example, titrating BRCA1 expression may enhance HDR as it has been shown to inhibit the pro-NHEJ/anti-HDR role of 53BP1, resulting in greater activity of pro-HDR factors like CtIP at DSB sites.

Plasmids with the cDNA or mRNA encoding these factors could be transfected to transiently and globally upregulate these factors in cells.

Method #4: Recruitment or Blocking of DNA Repair Factors at the Site of a Nuclease-Induced DSB to Enhance HDR 4a: Recruitzment of HDR-Associated Factors The specific components of the two predominant DNA-repair pathways in cells (NHEJ or HDR) have been well studied, allowing individual components of either mechanism to be either recruited or blocked to influence the nature of the repair outcome. A customized nuclease (e.g., ZFN, TALEN, Cas9 nucleases, Cas9 nickases, CRISPR RNA-guided FokI nucleases) can be used to generate targeted DSBs while simultaneously recruiting HDR factors to or blocking NHEJ factors from the same genomic site.

DNA-repair via HDR involves multiple classes of proteins that include nucleases or helicases to process free DNA ends, and protein binding domains to act as nucleation sites for supplementary HDR factors. Examples of each class of HDR-related protein (and post-translationally modified derivatives of these factors) include but are not limited to the following:

1) Nucleases and/or helicases that promote DNA strand resection a. MRE11—a critical component of the MRN (Mre11-Rad50-Nbs1) complex that completes initial end resection of free DNA-ends following DSBs. MRE11 is a 3'-to-5' exonuclease that also has endonuclease activity on ssDNA substrates, and has a preference for blunt DNA-ends (the most common product of Cas9 nuclease activity).

b. EXO1—suggested to act in concert with the MRN complex, EXO1 possesses 5'-to-3' exonuclease activity to initiate long resection of dsDNA ends to generate 3'-overhangs desirable for HDR-driven repair.

c. DNA2—a conserved helicase/5'-to-3' exonuclease that is also involved in the long resection process similar to EXO1.

d. CtIP—recruited by and works cooperatively with the MRN complex to initiate resection along with MRE11. Also known to antagonize the binding of pro-NHEJ factors such as 53BP1 or RIF1.

e. Modified CtIP—the activities of many components of the HDR pathway are regulated by post-translational modifications (PTMs), such as phosphorylation or acetylation, in a cell-cycle-specific manner. For instance, CtIP is phosphorylated at the T847 and S327 residues and deacetylated at K432, K526, and K604 during the S and G2 phases of the cell cycle. These PTMs restrict CtIP activity in HDR to S and G2. To overcome these restrictions, a modified form of CtIP bearing the amino acid substitutions T847E, S327E, K432R, K526R, and K604R, in any combination or together, may be recruited to DSBs through the aforementioned means. These modifications overcome the PTM restrictions by mimicking, in the case of T847E and S327E, the constitutively active form of CtIP. Conversely, K432R, K526R, and K604R mimick CtIP's constitutively active state by preventing acetylation at these positions.

f. TREX2—a 3' exonuclease that has been shown to increase gene disruption rates when overexpressed with engineered nucleases.

g. Apollo—a 5' exonuclease that protects telomeres by acting antagonistically to NHEJ-repair events.

2) Binding factors/nucleation proteins that recruit specific factors or catalyze strand invasion a. BRCA1—a factor that acts early in the HDR pathway to mediate interactions with HDR-specific proteins. BRCA1 has been shown to bind and recruit each component of the MRN complex as well as CtIP, all of which can initiate strand resection to create HDR template ends. Also, during S-phase will exclude pro-NHEJ factors from the sites of DSBs.

b. BRCA2—contains numerous RAD51 binding sites and has been implicated in RAD51 filament formation by assisting loading onto RPA coated ssDNA.

c. PALB2—a mediator protein that bridges the interactions between BRCA1 and BRCA2 and effectively promotes BRCA2 recruitment to DSB sites. Shown to interact with ssDNA and directly interact with RAD51 to stimulate strand invasion.

d. RAD50 or NBS1—RAD50 is a dimeric protein that binds to MRE11 and NBS1 to form the MRN complex that is critical to tether DSB ends prior to repair pathway selection. RAD50 fusions could act as a structural scaffold to recruit factors involved at very early stages of the DNA repair pathways. NBS1 forms foci at DSBs and therefore serves a similar recruiting role as RAD50, with additional roles in checkpoint signaling.

e. RAD51—a recombinase that assembles as a nucleofilament protein onto ssDNA 3'-overhangs to invade homologous donor DNA sequences to drive HDR repair.

f. Modified RAD51—RAD51 is phosphorylated at the T309 residue during the S and G2 phases of the cell cycle. Phosphorylation at this residue is critical to the ability of RAD51 to form filaments near DSBs. Mutating T309 to T309E mimics RAD51's constitutively active form. Recruitment of RAD51 bearing the T309E mutation to DSBs through any of the aforementioned means may serve to increase HDR activity.

g. RAD52—binds both ssDNA and dsDNA to form an oligomeric ring complex to catalyze annealing of complementary strands. RAD52 fusions should be able to enhance HDR when donor DNA is present as ssDNA or dsDNA in excess via transfection, tethered as in Example #1 above, or when hybrid gRNA/ssDNA molecules are used (as described above in Example #1).

h. RAD54—factor with conserved helicase motifs that is involved in recombination by modifying DNA topology. Also contains RAD51 binding sites.

i. SRCAP—a chromatin remodeling factor that promotes the accumulation of CtIP at DSBs and enhances CtIP-dependent DNA-end resection.

j. FANCI and FANCD2—Recruit downstream Fanconi Anemia Intercrosslink Repair Pathway proteins to a double strand break site to perform homologous repair. FancI and FancD2 are monoubiquitinated in order to localize to the double strand break, but it is possible that the activity of the complex may not rely on ubiquitination (Kim and D'Andrea, Genes Dev. 2012 Jul. 1; 26(13):1393-408). Both the monoubiquitinated and unmodified complex will be utilized to recruit HDR factors at the double strand break site.

k. BRIP1 (FANCJ), SLX4 (FANCP), FANCA, FANCE, FANCL and aforementioned RAD51C (FANCO), BRCA2 (FANCD1), PALB2 (FANCN)-Downstream proteins of the Fanconi Anemia Interstrand Crosslink Repair Pathway that are recruited to or enhance the activity of the monoubiquitinated FANCD2/FANCI protein complex at DSB sites. These proteins will be recruited simultaneously or separately in order to promote HDR at the double strand break site.

Figure 3E:
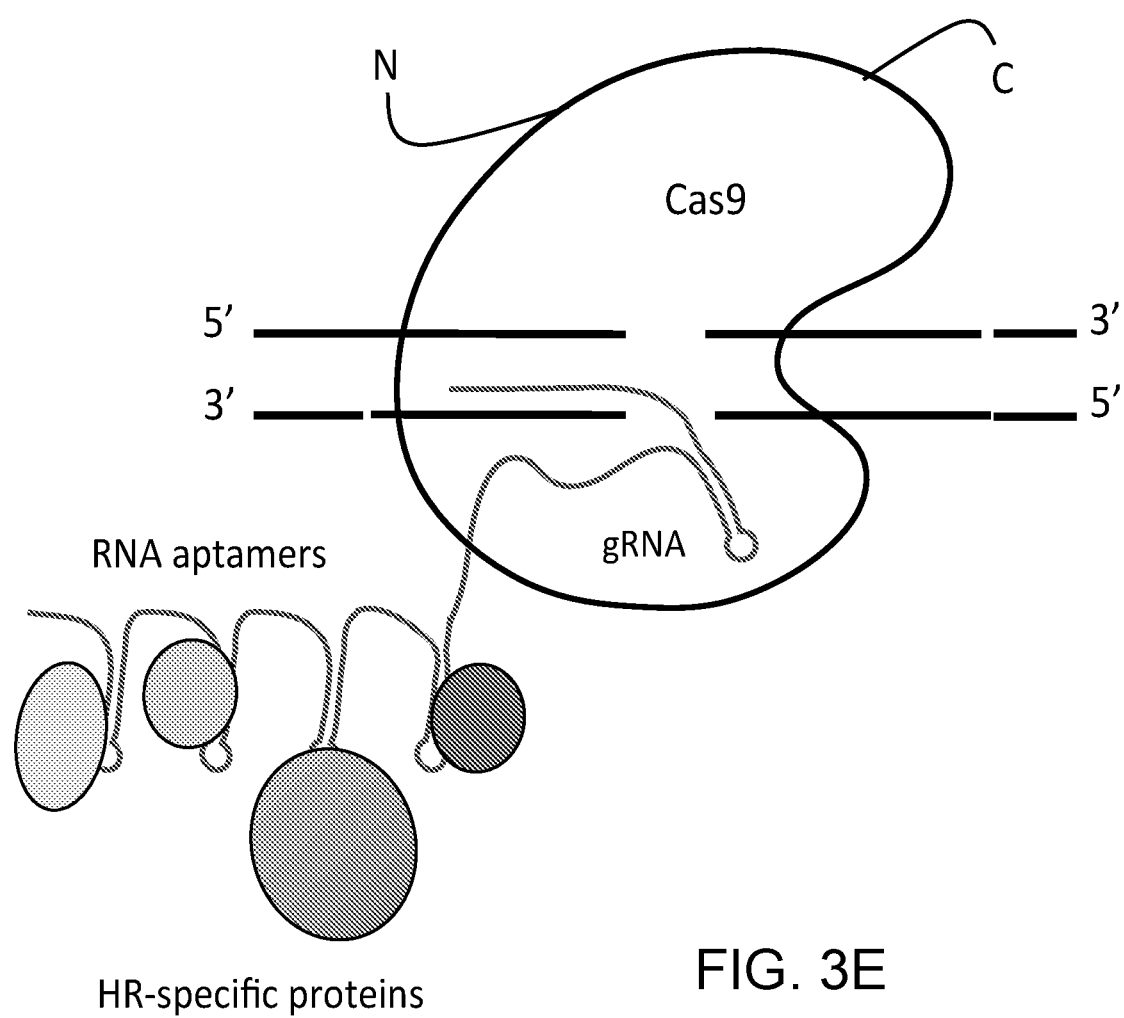
FIGS. 3E-F show exemplary schematics for recruitment of HR-specific factors to nuclease induced DSB. (e) Direct fusion of RNA aptamers to the 3' end of the gRNA directing a Cas9 nuclease. The aptamers bind with high specificity to HDR-associated factors and recruit these factors to the cleavage site induced by the Cas9 nuclease. (f) Direct fusion of distinct sets of RNA aptamers to each of the paired gRNAs used to direct CRISPR RNA-guided FokI nucleases.
Figure 3F:
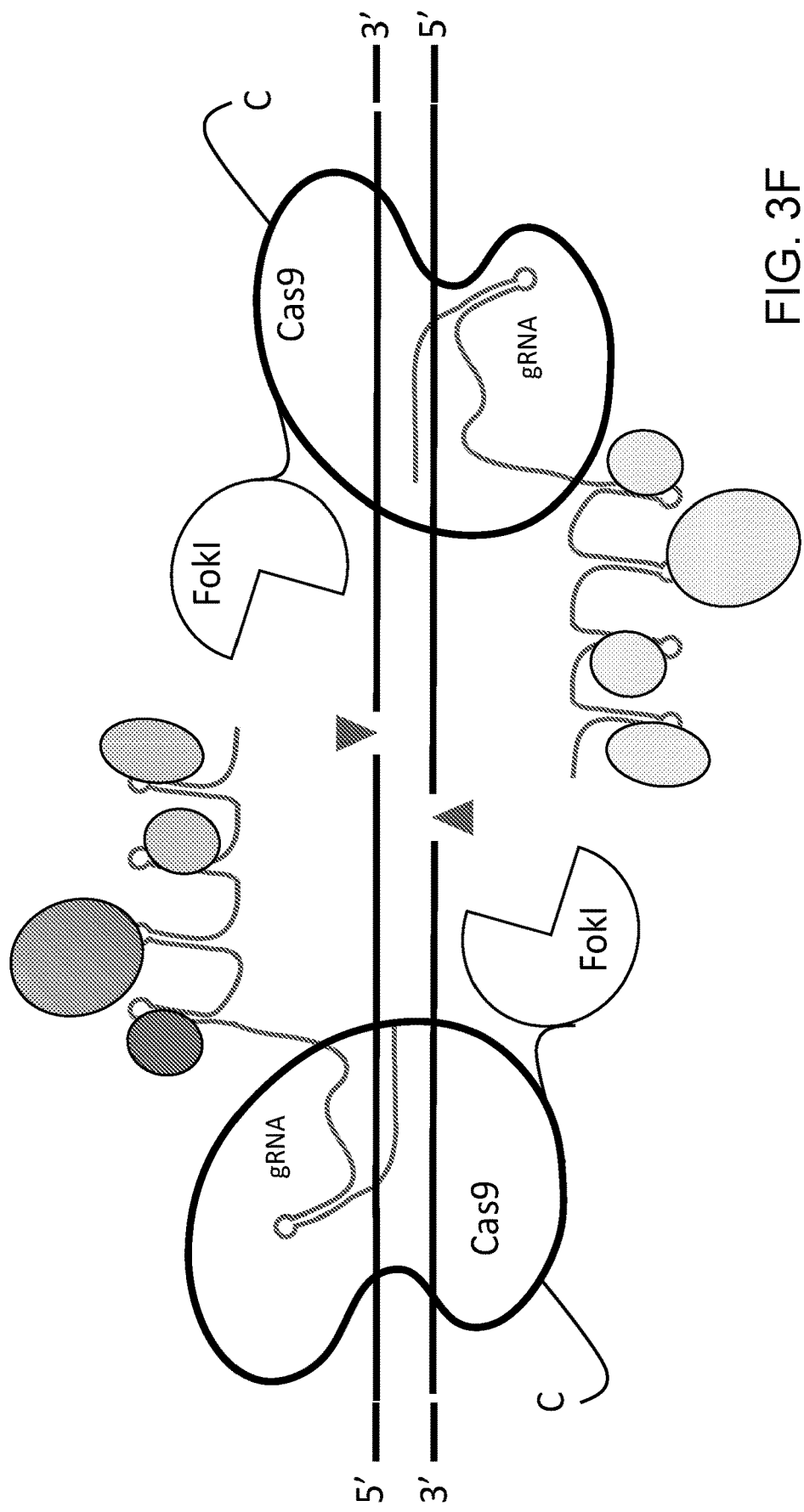

To enhance HDR, full length or truncated versions of any of the HDR-associated factors described here can be fused to either customized nucleases (FIG. 3b) or to a DBD that binds, e.g., is designed to bind, adjacent to the nuclease-induced DSB. As an alternative to covalently fusing these factors, they might also be directed to interact with a customized nuclease or an DBD via dimerization domains (FIG. 3c). In some instances, these dimerization domains might constitutively interact or interact in a temporally-restricted inducible fashion using either small molecule- or light-activated dimerization domains. Additionally, multiple distinct HDR factors could be recruited to the nuclease or DBD simultaneously (for example, Mre11, Rad50, and Nbs1 along with CtIP could all be localized to reconstitute the active MRN-CtIP complex). Alternatively, for Cas9 nucleases, Cas9 nickases, and/or CRISPR RNA-guided FokI nucleases, these HDR-associated factors might be fused to an RNA-binding protein (such as MS2 or Csy4) that can interact with a specific RNA sequence appended to the end of a guide RNA sequence (FIG. 3d). We note that various factors or dimerization domains might be fused to the customized nuclease AND a DBD in various combinations to induce HDR. Alternatively, RNA aptamers that bind specific HDR-associated factors might be fused to the 3' end of the gRNA as single aptamers or in a combinatorial fashion to recruit these factors to a DSB (FIGS. 3e-f). In the case of CRISPR RNA-guided FokI nucleases, the aptamers fused to one gRNA might differ from those fused to its paired gRNA, allowing for greater combinatorial recruitment of factors.

Additionally, any of the pro-HDR or anti-NHEJ factors listed herein can be overexpressed in the cell from a plasmid (as individual factors or combinations of factors) without covalent tethering to a nuclease, DBD, dimerization domain, or RNA-binding protein.

4b: Blocking of NHEJ-Associated Factors

Error-prone NHEJ is the dominant DSB repair pathway in mammalian cells, is available during all phases of the cell cycle, and can repair DSBs with faster kinetics than the HDR pathway. One factor limiting the efficiency of HDR may be the rapid binding of Ku70, an NHEJ-factor, to DSBs, and the subsequent recruitment of DNA-dependent protein kinase (DNA-PK), 53BP1 (also called Tumor Protein P53 Binding Protein 1 or TP53BP1), and other critical components of the NHEJ machinery.

One approach to increase the efficiency of HDR includes recruitment of defective NHEJ machinery components, such as a version of DNA-PK that interact and bind Ku70 but is impaired for recruitment of one or more end-processing factors such as Artemis, polynucleotide kinase/phosphatase (PNKP), AP endonuclease 1 (APE1) and tyrosyl-DNA phosphodiesterase (TDP1).

53BP1 is also known to be a major regulator of DNA repair pathway choice. Recent studies have identified RAP1-interacting factor (Rif1) as an ATM phosphorylation-dependent interactor of 53BP1 that is the main factor used by 53BP1 to block 5' end resection. One approach to impairing 53BP1 function would be to locally supply a defective version of Rif1. Additionally, it would be possible to down-regulate the expression of endogenous pro-NHEJ factors (including, but not limited to 53BP1) by targeting transcriptional repressors composed of KRAB or SID domains fused to dCas9 or other DBDs.

These strategies locally interfere with the canonical NHEJ pathway, thereby providing greater opportunity for 5' end resection and homology directed repair to occur.

Method #5: Enhancing HDR by Creating DSBs with 3' Overhangs

FokI-based nucleases such as ZFNs, TALENs, and recently described CRISPR RNA-guided FokI-nucleases (RFNs or fCas9) induce double-stranded breaks with a 4-nucleotide 5' overhang; however, homology directed repair is initiated by 5'→3' end resection of DSBs, resulting in 3' overhangs that are substrates for binding of RAD51 and that can interact further with the HDR machinery. Using nucleases that leave 3' overhangs is expected to create DSBs that will more likely be repaired by HDR rather than NHEJ.

A number of strategies could be used to create such overhangs:

(1) Using pairs of appropriately positioned engineered nickases (either ZFNickases or Cas9 nickases) whose concerted action would lead to the formation of a DSB with 3' overhangs. This includes, but is not limited to, H840A or N863A Cas9 HNH domain inactivating mutations (FIG. 4).

(2) Modifying existing ZFN, TALEN, or CRISPR RNA-guided FokI nuclease architectures by replacing existing FokI domains (which leave 5' overhangs) with dimerization-dependent nuclease domains that make DSBs with 3' overhangs. Nuclease domains that leave 3' overhangs can be derived, e.g., from a restriction enzyme that leaves a 3' overhang, e.g., KpnI, HHaI, MnlI, NlaIII, BspCNI, BsrI, BtsCI, HphI, PvuII, SacI, and so on.

(3) Using FokI-dCas9 proteins that comprise a FokI cleavage domain fused to a H840-Cas9 nickase (or N863A-Cas9 nickase). Recruitment of this variant by two appropriate spaced guide RNAs would be expected to generate a DSB with 3' overhangs (see FIG. 5). This hybrid architecture is predicted to introduce 2 nicks and a DSB at a defined target site, leaving long 3' overhangs that could serve as ideal substrates for HDR (see FIG. 5).

Method #6: Enhancing HDR by fusions of engineered DNA binding domains to Spo11

Spo11 generates DSBs in meiotic cells, is required for synapsis, and remains covalently bound to DSBs after cleavage. It is believed that Mre11 exonuclease may process Spo11-bound DSBs to produce 3' ends that are ideal substrates for HDR. One strategy for enhancing HDR then would be to fuse an engineered DNA binding domain (ZF, TALE, dCas9/gRNA) to Spo11 (in either N-, C-, or internal fusions) to DNA with appropriate spacing. This would be performed by targeting a pair of DBD-Spo11 monomers with appropriate spacing to create targeted DSBs with 3' overhangs.

The sequence of human Spo11 isoform A is as follows:

(SEQ ID NO: 6)
MAFAPMGPEASFFDVLDRHRESLLAALRRGGREPPTGGSRLASSSEVLAS

IENIIQDIITSLARNEAPAFTIDNRSSWENIKFEDSVGLQMVSHCTTRKI

KSDSPKSAQKFSLILKILSMIYKLVQSNTYATKRDIYYTDSQLFGNQTVV

DNIINDISCMLKVSRRSLHILSTSKGLIAGNLRYIEEDGTKVNCTCGATA

-continued
VAVPSNIQGIRNLVTDAKFVLIVEKDATFQRLLDDNFCNKLSPCIMITGK

GVPDLNTRLLVKKLWDTFHVPVFTLVDADPHGIEIMCIYKYGSMSMSFEA

HHLTVPAIRWLGLLPSDLKRLNVPKDSLIPLTKRDQMKLDSILRRPYVTC

QPFWRKEMEIMADSKMKAEIQALTFLSSDYLSRVYLPNKLKFGGWI

The sequence of human Spo11 isoform B is as follows:

(SEQ ID NO: 7)
MAFAPMGPEASFFDVLDRHRESLLAALRRGGREPPTGGSRLASRFEDSVG

LQMVSHCTTRKIKSDSPKSAQKFSLILKILSMIYKLVQSNTYATKRDIYY

TDSQLFGNQTVVDNIINDISCMLKVSRRSLHILSTSKGLIAGNLRYIEED

GTKVNCTCGATAVAVPSNIQGIRNLVTDAKFVLIVEKDATFQRLLDDNFC

NKLSPCIMITGKGVPDLNTRLLVKKLWDTFHVPVFTLVDADPHGIEIMCI

YKYGSMSMSFEAHHLTVPAIRWLGLLPSDLKRLNVPKDSLIPLTKRDQMK

LDSILRRPYVTCQPFWRKEMEIMADSKMKAEIQALTFLSSDYLSRVYLPN

KLKFGGWI

Thus, provided herein are Spo11-DBD fusion proteins with a DBD as described herein fused to the C terminus or N terminus of Spo11, optionally with an intervening linker sequence of 1-50 amino acids.

Method #7: Enhancing HDR by Targeted Chromatin Modifications.

Recent evidence suggests that the chromatin context of a DSB may also influence repair pathway choice. For example, LEDGF, bound to H3K36me3, can recruit CtIP, a factor critical for end resection. Thus, provided herein are fusions of chromatin modifiers including, but not limited to SETD2, SRCAP, and SMARCAD1 to determine whether initiation of end resection and ultimately DNA repair outcomes can be biased in favor of HDR. Chromatin modifying proteins or domains may be fused directly to Cas9 or other DBDs, or localized via aforementioned dimerization/recruitment approaches.

Method #8: Enhancing HDR with In Vitro Produced Protein-Bound Donor Templates

It has been recently reported that nuclease-mediated gene targeting using protein-capped adenoviral donor vectors (Holkers et al., Nat Methods. 2014 October; 11(10):1051-7) results in precise repair with higher frequencies than with free-ended integration-defective lentiviral vectors (IDLV) or plasmid donors. This result was shown to depend on protein capping of the adenoviral donor DNA. In vitro studies in yeast have also shown that (Cannavo et al. Nature 2014) the MRX-mediated resection of DNA is stimulated by the presence of protein blocks on the DNA ends. We envision the use of simple donor templates created by PCR using 5'- or 3'-biotinylated primers and associated with streptavidin, resulting in a protein-capped donor template.

DNA-Binding Domains

The fusion proteins described herein can include any DNA Binding Domain (DBD) known in the art or engineered for a specific binding site. Exemplary DBDs include engineered or native TAL effector repeat arrays, engineered or native zinc fingers, modified variants (e.g., catalytically inactive) of homing meganucleases, modified variants (e.g., catalytically inactive) nucleases from the CRISPR-Cas system, chemical nucleases, and other native DBDs.

TAL Effector Repeat Arrays

TAL effectors of plant pathogenic bacteria in the genus *Xanthomonas* play important roles in disease, or trigger defense, by binding host DNA and activating effector-specific host genes. Specificity depends on an effector-variable number of imperfect, typically ~33-35 amino acid repeats. Polymorphisms are present primarily at repeat positions 12 and 13, which are referred to herein as the repeat variable-diresidue (RVD). The RVDs of TAL effectors correspond to the nucleotides in their target sites in a direct, linear fashion, one RVD to one nucleotide, with some degeneracy and no apparent context dependence. In some embodiments, the polymorphic region that grants nucleotide specificity may be expressed as a triresidue or triplet.

Each DNA binding repeat can include a RVD that determines recognition of a base pair in the target DNA sequence, wherein each DNA binding repeat is responsible for recognizing one base pair in the target DNA sequence. In some embodiments, the RVD can comprise one or more of: HA for recognizing C; ND for recognizing C; HI for recognizing C; HN for recognizing G; NA for recognizing G; SN for recognizing G or A; YG for recognizing T; and NK for recognizing G, and one or more of: HD for recognizing C; NG for recognizing T; NI for recognizing A; NN for recognizing G or A; NS for recognizing A or C or G or T; N* for recognizing C or T, wherein * represents a gap in the second position of the RVD; HG for recognizing T; H* for recognizing T, wherein * represents a gap in the second position of the RVD; and IG for recognizing T.

TALE proteins may be useful in research and biotechnology as targeted chimeric nucleases that can facilitate homologous recombination in genome engineering (e.g., to add or enhance traits useful for biofuels or biorenewables in plants). These proteins also may be useful as, for example, transcription factors, and especially for therapeutic applications requiring a very high level of specificity such as therapeutics against pathogens (e.g., viruses) as non-limiting examples.

Methods for generating engineered TALE arrays are known in the art, see, e.g., the fast ligation-based automatable solid-phase high-throughput (FLASH) system described in U.S. Ser. No. 61/610,212, and Reyon et al., Nature Biotechnology 30, 460-465 (2012); as well as the methods described in Bogdanove & Voytas, Science 333, 1843-1846 (2011); Bogdanove et al., Curr Opin Plant Biol 13, 394-401 (2010); Scholze & Boch, J. Curr Opin Microbiol (2011); Boch et al., Science 326, 1509-1512 (2009); Moscou & Bogdanove, Science 326, 1501 (2009); Miller et al., Nat Biotechnol 29, 143-148 (2011); Morbitzer et al., T. Proc Natl Acad Sci USA 107, 21617-21622 (2010); Morbitzer et al., Nucleic Acids Res 39, 5790-5799 (2011); Zhang et al., Nat Biotechnol 29, 149-153 (2011); Geissler et al., PLoS ONE 6, e19509 (2011); Weber et al., PLoS ONE 6, e19722 (2011); Christian et al., Genetics 186, 757-761 (2010); Li et al., Nucleic Acids Res 39, 359-372 (2011); Mahfouz et al., Proc Natl Acad Sci USA 108, 2623-2628 (2011); Mussolino et al., Nucleic Acids Res (2011); Li et al., Nucleic Acids Res 39, 6315-6325 (2011); Cermak et al., Nucleic Acids Res 39, e82 (2011); Wood et al., Science 333, 307 (2011); Hockemeye et al. Nat Biotechnol 29, 731-734 (2011); Tesson et al., Nat Biotechnol 29, 695-696 (2011); Sander et al., Nat Biotechnol 29, 697-698 (2011); Huang et al., Nat Biotechnol 29, 699-700 (2011); and Zhang et al., Nat Biotechnol 29, 149-153 (2011); all of which are incorporated herein by reference in their entirety.

Zinc Fingers

Zinc finger proteins are DNA-binding proteins that contain one or more zinc fingers, independently folded zinc-containing mini-domains, the structure of which is well known in the art and defined in, for example, Miller et al., 1985, EMBO J., 4:1609; Berg, 1988, Proc. Natl. Acad. Sci. USA, 85:99; Lee et al., 1989, Science. 245:635; and Klug, 1993, Gene, 135:83. Crystal structures of the zinc finger protein Zif268 and its variants bound to DNA show a semi-conserved pattern of interactions, in which typically three amino acids from the alpha-helix of the zinc finger contact three adjacent base pairs or a "subsite" in the DNA (Pavletich et al., 1991, Science, 252:809; Elrod-Erickson et al., 1998, Structure, 6:451). Thus, the crystal structure of Zif268 suggested that zinc finger DNA-binding domains might function in a modular manner with a one-to-one interaction between a zinc finger and a three-base-pair "subsite" in the DNA sequence. In naturally occurring zinc finger transcription factors, multiple zinc fingers are typically linked together in a tandem array to achieve sequence-specific recognition of a contiguous DNA sequence (Klug, 1993, Gene 135:83).

Multiple studies have shown that it is possible to artificially engineer the DNA binding characteristics of individual zinc fingers by randomizing the amino acids at the alpha-helical positions involved in DNA binding and using selection methodologies such as phage display to identify desired variants capable of binding to DNA target sites of interest (Rebar et al., 1994, Science, 263:671; Choo et al., 1994 Proc. Natl. Acad. Sci. USA, 91:11163; Jamieson et al., 1994, Biochemistry 33:5689; Wu et al., 1995 Proc. Natl. Acad. Sci. USA, 92: 344). Such recombinant zinc finger proteins can be fused to functional domains, such as transcriptional activators, transcriptional repressors, methylation domains, and nucleases to regulate gene expression, alter DNA methylation, and introduce targeted alterations into genomes of model organisms, plants, and human cells (Carroll, 2008, Gene Ther., 15:1463-68; Cathomen, 2008, Mol. Ther., 16:1200-07; Wu et al., 2007, Cell. Mol. Life Sci., 64:2933-44).

Widespread adoption and large-scale use of zinc finger protein technology have been hindered by the continued lack of a robust, easy-to-use, and publicly available method for engineering zinc finger arrays. One existing approach, known as "modular assembly," advocates the simple joining together of pre-selected zinc finger modules into arrays (Segal et al., 2003, Biochemistry, 42:2137-48; Beerli et al., 2002, Nat. Biotechnol., 20:135-141; Mandell et al., 2006, Nucleic Acids Res., 34:W516-523; Carroll et al., 2006, Nat. Protoc. 1:1329-41; Liu et al., 2002, J. Biol. Chem., 277: 3850-56; Bae et al., 2003, Nat. Biotechnol., 21:275-280; Wright et al., 2006, Nat. Protoc., 1:1637-52). Although straightforward enough to be practiced by any researcher, recent reports have demonstrated a high failure rate for this method, particularly in the context of zinc finger nucleases (Ramirez et al., 2008, Nat. Methods, 5:374-375; Kim et al., 2009, Genome Res. 19:1279-88), a limitation that typically necessitates the construction and cell-based testing of very large numbers of zinc finger proteins for any given target gene (Kim et al., 2009, Genome Res. 19:1279-88).

Combinatorial selection-based methods that identify zinc finger arrays from randomized libraries have been shown to have higher success rates than modular assembly (Maeder et al., 2008, Mol. Cell, 31:294-301; Joung et al., 2010, Nat. Methods, 7:91-92; Isalan et al., 2001, Nat. Biotechnol., 19:656-660; Sander et al., Nat Methods. 8(1):67-9, 2011; Bhakta et al., Genome Res. 23(3):530-8, 2013). In preferred embodiments, the zinc finger arrays are described in, or are generated as described in, WO 2011/017293 and WO 2004/099366. Additional suitable zinc finger DBDs are described in U.S. Pat. Nos. 6,511,808, 6,013,453, 6,007,988, and 6,503,717 and U.S. patent application 2002/0160940.

Native DBDs

In some embodiments, a native DBD (e.g., a portion of a wild-type, non-engineered DNA binding protein that binds to a specific target sequence) can be used. For example, the DBD from a transcription factor, nuclease, histone, telomerase, or other DNA binding protein can be used. Typically DBDs include a structure that facilitates specific interaction with a target nucleic acid sequence; common DBD structures include helix-turn-helix; zinc finger; leucine zipper; winged helix; winged helix turn helix; helix-loop-helix; and hmg-box. The native DBD can be from any organism. See, e.g., Kummerfeld & Teichmann, Nucleic Acids Res. 34 (Database issue): D74-81 (2006). The residues in a DNA binding protein that contact DNA, and thus form part of the DBD, can be determined empirically or predicted computationally, e.g., as described in Tjong and Zhou, Nucl. Acids Res. 35:1465-1477 (2007). A database of DNA binding proteins can be used to identify DNA binding proteins and DBDs for use in the present compositions and methods; see, e.g., Harrison, Nature, 353, 715-719 (1991); Karmirantzou and Hamodrakas, Protein Eng. 14(7): 465-472 (2001); Kumar et al., BMC Bioinformatics. 8:463 (2007); Kumar et al., J Biomol Struct Dyn. 26(6):679-86 (2009); Lin et al., PLoS One. 6(9):e24756 (2011).

Where a native DBD is used in a fusion protein described herein, the catalytic domain is from a different protein.

Homing Meganucleases

Meganucleases are sequence-specific endonucleases originating from a variety of organisms such as bacteria, yeast, algae and plant organelles. Endogenous meganucleases have recognition sites of 12 to 30 base pairs; customized DNA binding sites with 18 bp and 24 bp-long meganuclease recognition sites have been described, and either can be used in the present methods and constructs. See, e.g., Silva, G., et al., Current Gene Therapy, 11:11-27, (2011); Arnould et al., Journal of Molecular Biology, 355:443-58 (2006); Arnould et al., Protein Engineering Design & Selection, 24:27-31 (2011); and Stoddard, Q. Rev. Biophys. 38, 49 (2005); Grizot et al., Nucleic Acids Research, 38:2006-18 (2010). In some embodiments, catalytically inactive versions of the homing meganucleases are used, e.g., a mutant of I-SceI, e.g., comprising the mutation D44S, wherein the catalytically active aspartate from the first LAGLIDADG motif is mutated to serine to make the enzyme inactive; N152K, reported to have ~80% of the wt-activity; or the double variant D150C/N152K, which decreases the activity of the enzyme even further, e.g., as described in Gruen et al., Nucleic Acids Res. 2002; 30:e29; Fonfara et al., Nucleic Acids Res. 2012 January; 40(2): 847-860; and Lippow et al., Nucleic Acids Res. 2009 May; 37(9):3061-73.

Cas9

Catalytically inactive versions of the Cas9 nuclease can also be used as DBDs in the fusion proteins described herein; these fusion proteins are used in combination with a single guide RNA or a crRNA/tracrRNA pair for specificity. A number of bacteria express Cas9 protein variants. The Cas9 from *Streptococcus pyogenes* is presently the most commonly used; some of the other Cas9 proteins have high levels of sequence identity with the *S. pyogenes* Cas9 and use the same guide RNAs. Others are more diverse, use different gRNAs, and recognize different PAM sequences as well (the 2-5 nucleotide sequence specified by the protein which is adjacent to the sequence specified by the RNA). Chylinski et al. classified Cas9 proteins from a large group of bacteria (RNA Biology 10:5, 1-12; 2013), and a large number of Cas9 proteins are listed in supplementary FIG. 1 and supplementary table 1 thereof, which are incorporated by reference herein. The constructs and methods described herein can include the use of any of those Cas9 proteins, and their corresponding guide RNAs or other guide RNAs that are compatible. The Cas9 from *Streptococcus thermophilus* LMD-9 CRISPR1 system has also been shown to function in human cells in Cong et al (Science 339, 819 (2013)). Additionally, Jinek et al. showed in vitro that Cas9 orthologs from *S. thermophilus* and *L. innocua*, (but not from *N. meningitidis* or *C. jejuni*, which likely use a different guide RNA), can be guided by a dual *S. pyogenes* gRNA to cleave target plasmid DNA, albeit with slightly decreased efficiency. These proteins are preferably mutated such that they retain their ability to be guided by the single guide RNA or a crRNA/tracrRNA pair and thus retain target specificity, but lack nuclease activity.

In some embodiments, the present system utilizes the Cas9 protein from *S. pyogenes*, either as encoded in bacteria or codon-optimized for expression in mammalian cells, containing mutations to render the nuclease portion of the protein catalytically inactive, e.g., mutations at D10, E762, H983, or D986; and at H840 or N863, e.g., at D10 and H840, e.g., D10A or D1ON and H840A or H840N or H840Y.; see, e.g., Jinek et al., Science 2012; 337:816-821; Qi et al., Cell 152, 1173-1183 (2013).

Chemical Nucleases

DNA binding domains from the so-called "chemical nucleases," (Pingoud and Silva, Nat Biotechnol. 25:743-4 (2007)), e.g., triplex-forming oligonucleotides or peptide nucleic acids can also be utilized in the present compositions and methods; see, e.g., Schleifman et al., Methods Mol Biol. 2008; 435:175-90; Arimondo et al., Mol Cell Biol. 2006 January; 26(1):324-33; Majumdar et al., J Biol Chem. 2008 Apr. 25; 283(17):11244-52; Simon et al., Nucleic Acids Res. 2008 June; 36(11):3531-8; or Eisenschmidt et al., Nucleic Acids Res. 2005; 33(22):7039-47.

Nucleases

The fusion proteins described herein can include any nuclease known in the art. Exemplary nucleases include engineered TALENs, zinc finger nucleases (ZFNs), homing meganucleases, nucleases from the CRISPR-Cas system, and other chemical nucleases. In some embodiments, a catalytically active nuclease domain is used, e.g., a Fok I cleavage domain. Some of the nuclease systems are described generally in Gaj et al., Trends Biotechnol. 2013 July; 31(7):397-405; Kim and Kim, Nat Rev Genet. 2014 May; 15(5):321-34;

TALEN

Transcription activator-like effector nucleases (TALENs) comprise a nonspecific DNA-cleaving nuclease (e.g., a Fok I cleavage domain) fused to a DNA-binding domain that can be easily engineered so that TALENs can target essentially any sequence (See, e.g., Joung and Sander, Nature Reviews Molecular Cell Biology 14:49-55 (2013)). Methods for generating engineered TALENs are known in the art, see, e.g., the fast ligation-based automatable solid-phase high-throughput (FLASH) system described in U.S. Ser. No. 61/610,212, and Reyon et al., Nature Biotechnology 30, 460-465 (2012); as well as the methods described in Bogdanove & Voytas, Science 333, 1843-1846 (2011); Bogdanove et al., Curr Opin Plant Biol 13, 394-401 (2010); Scholze & Boch, J. Curr Opin Microbiol (2011); Boch et al., Science 326, 1509-1512 (2009); Moscou & Bogdanove, Science 326, 1501 (2009); Miller et al., Nat Biotechnol 29, 143-148 (2011); Morbitzer et al., T. Proc Natl Acad Sci USA 107, 21617-21622 (2010); Morbitzer et al., Nucleic Acids Res 39, 5790-5799 (2011); Zhang et al., Nat Biotechnol 29, 149-153 (2011); Geissler et al., PLoS ONE 6, e19509 (2011); Weber et al., PLoS ONE 6, e19722 (2011); Christian et al., Genetics 186, 757-761 (2010); Li et al., Nucleic Acids Res 39, 359-372 (2011); Mahfouz et al., Proc Natl Acad Sci USA 108, 2623-2628 (2011); Mussolino et al., Nucleic Acids Res (2011); Li et al., Nucleic Acids Res 39, 6315-6325 (2011); Cermak et al., Nucleic Acids Res 39, e82 (2011); Wood et al., Science 333, 307 (2011); Hockemeye et al. Nat Biotechnol 29, 731-734 (2011); Tesson et al., Nat Biotechnol 29, 695-696 (2011); Sander et al., Nat Biotechnol 29, 697-698 (2011); Huang et al., Nat Biotechnol 29, 699-700 (2011); and Zhang et al., Nat Biotechnol 29, 149-153 (2011); all of which are incorporated herein by reference in their entirety.

ZFN

Zinc-finger nucleases (ZFNs) are composed of programmable, sequence-specific zinc finger DNA-binding modules (see above) linked to a nonspecific DNA cleavage domain, e.g., a Fok I cleavage domain. Methods for making and using ZFNs are known in the art, see, e.g., (Maeder et al., 2008, Mol. Cell, 31:294-301; Joung et al., 2010, Nat. Methods, 7:91-92; Isalan et al., 2001, Nat. Biotechnol., 19:656-660; Sander et al., Nat Methods. 8(1):67-9, 2011; Bhakta et al., Genome Res. 23(3):530-8, 2013). In some embodiments, the ZFNs are described in, or are generated as described in, WO 2011/017293 or WO 2004/099366. Additional suitable ZFNs are described in U.S. Pat. Nos. 6,511, 808, 6,013,453, 6,007,988, and 6,503,717 and U.S. patent application 2002/0160940.

Meganucleases

As noted above, meganucleases are sequence-specific endonucleases originating from a variety of organisms such as bacteria, yeast, algae and plant organelles. A number of Meganucleases are known in the art, see, e.g., WO 2012010976 (Meganuclease variants cleaving DNA target sequences of the TERT gene); U.S. Pat. Nos. 8,021,867; 8,119,361 and 8,119,381 (I-CreI meganucleases); U.S. Pat. No. 7,897,372 (I-CreI Meganuclease Variants with Modified Specificity).

CRISPR/Cas System

Clustered, regularly interspaced, short palindromic repeats (CRISPR)/CRISPR-associated (Cas) systems (Wiedenheft et al., Nature 482, 331-338 (2012); Horvath et al., Science 327, 167-170 (2010); Terns et al., Curr Opin Microbiol 14, 321-327 (2011)) can serve as the basis for performing genome editing in bacteria, yeast and human cells, as well as in vivo in whole organisms such as fruit flies, zebrafish and mice (Wang et al., Cell 153, 910-918 (2013); Shen et al., Cell Res (2013); Dicarlo et al., Nucleic Acids Res (2013); Jiang et al., Nat Biotechnol 31, 233-239 (2013); Jinek et al., Elife 2, e00471 (2013); Hwang et al., Nat Biotechnol 31, 227-229 (2013); Cong et al., Science 339, 819-823 (2013); Mali et al., Science 339, 823-826 (2013c); Cho et al., Nat Biotechnol 31, 230-232 (2013); Gratz et al., Genetics 194(4):1029-35 (2013)). The Cas nuclease, e.g., the Cas9 nuclease from *S. pyogenes* (hereafter simply Cas9), can be guided via base pair complementarity between the first 17-20 nucleotides of an engineered guide RNA (gRNA) and the complementary strand of a target genomic DNA sequence of interest that lies next to a protospacer adjacent motif (PAM), e.g., a PAM matching the sequence NGG or NAG (Shen et al., Cell Res (2013); Dicarlo et al., Nucleic Acids Res (2013); Jiang et al., Nat Biotechnol 31, 233-239 (2013); Jinek et al., Elife 2, e00471 (2013); Hwang et al., Nat Biotechnol 31, 227-229 (2013); Cong et al., Science 339, 819-823 (2013); Mali et al., Science 339, 823-826 (2013c); Cho et al., Nat Biotechnol 31, 230-232 (2013); Jinek et al., Science 337, 816-821 (2012)). See also Tsai et al., Nat Biotechnol. 2014 June; 32(6):569-76; Hwang et al., Nat Biotechnol. 2013 March; 31(3):227-9, U.S. Pat. No. 8,697,359; U.S. Ser. No. 14/213,723; and PCT/US2014/029068.

Chemical Nuclease

Chemical nucleases, e.g., triplex-forming oligonucleotides or peptide nucleic acids can also be utilized in the present compositions and methods; see above.

FokI

FokI is a type IIs restriction endonuclease that includes a DNA recognition domain and a catalytic (endonuclease) domain. The fusion proteins described herein can include all of FokI or just the catalytic endonuclease domain, e.g., amino acids 388-583 or 408-583 of GenBank Acc. No. AAA24927.1, e.g., as described in WO95/09233, Li et al., Nucleic Acids Res. 39(1): 359-372 (2011); Cathomen and Joung, Mol. Ther. 16: 1200-1207 (2008), or a mutated form of FokI as described in Miller et al. Nat Biotechnol 25: 778-785 (2007); Szczepek et al., Nat Biotechnol 25: 786-793 (2007); or Bitinaite et al., Proc. Natl. Acad. Sci. USA. 95:10570-10575 (1998). See also Tsai et al., Nat Biotechnol. 2014 June; 32(6):569-76.

An exemplary amino acid sequence of FokI is as follows:

```
                                                      (SEQ ID NO: 8)
         10         20         30         40         50         60
MFLSMVSKIR TFGWVQNPGK FENLKRVVQV FDRNSKVHNE VKNIKIPTLV KESKIQKELV 70         80         90        100        110        120
AIMNQHDLIY TYKELVGTGT SIRSEAPCDA IIQATIADQG NKKGYIDNWS SDGFLRWAHA 130        140        150        160        170        180
LGFIEYINKS DSFVITDVGL AYSKSADGSA IEKEILIEAI SSYPPAIRIL TLLEDGQHLT 190        200        210        220        230        240
KFDLGKNLGF SGESGFTSLP EGILLDTLAN AMPKDKGEIR NNWEGSSDKY ARMIGGWLDK 250        260        270        280        290        300
LGLVKQGKKE FIIPTLGKPD NKEFISHAFK ITGEGLKVLR RAKGSTKFTR VPKRVYWEML 310        320        330        340        350        360
ATNLTDKEYV RTRRALILEI LIKAGSLKIE QIQDNLKKLG FDEVIETIEN DIKGLINTGI 370        380        390        400        410        420
FIEIKGRFYQ LKDHILQFVI PNRGVTKQLV KSELEEKKSE LRHKLKYVPH EYIELIEIAR
```

```
       430        440        450        460        470        480
NSTQDRILEM KVMEFFMKVY GYRGKHLGGS RKPDGAIYTV GSPIDYGVIV DTKAYSGGYN 490        500        510        520        530        540
LPIGQADEMQ RYVEENQTRN KHINPNEWWK VYPSSVTEFK FLFVSGHFKG NYKAQLTRLN 550        560        570        580
HITNCNGAVL SVEELLIGGE MIKAGTLTLE EVRRKFNNGE INF
```

An exemplary nucleic acid sequence encoding FokI is as follows:

```
                                                      (SEQ ID NO: 9)
ATGTTTTTGAGTATGGTTTCTAAAATAAGAACTTTCGGTTGGGTTCAAAA

TCCAGGTAAATTTGAGAATTTAAAACGAGTAGTTCAAGTATTTGATAGAA

ATTCTAAAGTACATAATGAAGTGAAAAATATAAAGATACCAACCCTAGTC

AAAGAAAGTAAGATCCAAAAAGAACTAGTTGCTATTATGAATCAACATGA

TTTGATTTATACATATAAAGAGTTAGTAGGAACAGGAACTTCAATACGTT

CAGAAGCACCATGCGATGCAATTATTCAAGCAACAATAGCAGATCAAGGA

AATAAAAAAGGCTATATCGATAATTGGTCATCTGACGGTTTTTTGCGTTG

GGCACATGCTTTAGGATTTATTGAATATATAAATAAAAGTGATTCTTTTG

TAATAACTGATGTTGGACTTGCTTACTCTAAATCAGCTGACGGCAGCGCC

ATTGAAAAGAGATTTTGATTGAAGCGATATCATCTTATCCTCCAGCGAT

TCGTATTTTAACTTTGCTAGAAGATGGACAACATTTGACAAAGTTTGATC

TTGGCAAGAATTTAGGTTTTAGTGGAGAAAGTGGATTTACTTCTCTACCG

GAAGGAATTCTTTTAGATACTCTAGCTAATGCTATGCCTAAAGATAAAGG

CGAAATTCGTAATAATTGGGAAGGATCTTCAGATAAGTACGCAAGAATGA

TAGGTGGTTGGCTGGATAAACTAGGATTAGTAAAGCAAGGAAAAAAAGAA

TTTATCATTCCTACTTTGGGTAAGCCGGACAATAAAGAGTTTATATCCCA

CGCTTTTAAAATTACTGGAGAAGGTTTGAAAGTACTGCGTCGAGCAAAAG

GCTCTACAAAATTTACACGTGTACCTAAAAGAGTATATTGGGAAATGCTT

GCTACAAACCTAACCGATAAAGAGTATGTAAGAACAAGAAGAGCTTTGAT

TTTAGAAATATTAATCAAAGCTGGATCATTAAAAATAGAACAAATACAAG

ACAACTTGAAGAAATTAGGATTTGATGAAGTTATAGAAACTATTGAAAAT

GATATCAAAGGCTTAATTAACACAGGTATATTTATAGAAATCAAAGGGCG

ATTTTATCAATTGAAAGACCATATTCTTCAATTTGTAATACCTAATCGTG

GTGTGACTAAGCAACTAGTCAAAAGTGAACTGGAGGAGAAGAAATCTGAA

CTTCGTCATAAATTGAAATATGTGCCTCATGAATATATTGAATTAATTGA

AATTGCCAGAAATTCCACTCAGGATAGAATTCTTGAAATGAAGGTAATGG

AATTTTTTATGAAAGTTTATGGATATAGAGGTAAACATTTGGGTGGATCA

AGGAAACCGGACGGAGCAATTTATACTGTCGGATCTCCTATTGATTACGG

TGTGATCGTGGATACTAAAGCTTATAGCGGAGGTTATAATCTGCCAATTG

GCCAAGCAGATGAAATGCAACGATATGTCGAAGAAATCAAACACGAAAC

AAACATATCAACCCTAATGAATGGTGGAAAGTCTATCCATCTTCTGTAAC

GGAATTTAAGTTTTTATTTGTGAGTGGTCACTTTAAAGGAAACTACAAAG

CTCAGCTTACACGATTAAATCATATCACTAATTGTAATGGAGCTGTTCTT

AGTGTAGAAGAGCTTTTAATTGGTGGAGAAATGATTAAAGCCGGCACATT

AACCTTAGAGGAAGTGAGACGGAAATTTAATAACGGCGAGATAAACTTTT

AA
```

In some embodiments, the FokI nuclease used herein is at least about 50% identical SEQ ID NO:8, e.g., to amino acids 388-583 or 408-583 of SEQ ID NO:8. These variant nucleases must retain the ability to cleave DNA. In some embodiments, the nucleotide sequences are about 50%, 55%, 60%, 65%, 70%, 75%, 80%, 85%, 90%, 95%, 99% or 100% identical to amino acids 388-583 or 408-583 of SEQ ID NO:8. In some embodiments, any differences from amino acids 388-583 or 408-583 of SEQ ID NO:8 are in non-conserved regions.

To determine the percent identity of two sequences, the sequences are aligned for optimal comparison purposes (gaps are introduced in one or both of a first and a second amino acid or nucleic acid sequence as required for optimal alignment, and non-homologous sequences can be disregarded for comparison purposes). The length of a reference sequence aligned for comparison purposes is at least 50% (in some embodiments, about 50%, 55%, 60%, 65%, 70%, 75%, 85%, 90%, 95%, or 100% of the length of the reference sequence is aligned). The nucleotides or residues at corresponding positions are then compared. When a position in the first sequence is occupied by the same nucleotide or residue as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For purposes of the present application, the percent identity between two amino acid sequences is determined using the Needleman and Wunsch ((1970) J. Mol. Biol. 48:444-453) algorithm which has been incorporated into the GAP program in the GCG software package, using a Blossum 62 scoring matrix with a gap penalty of 12, a gap extend penalty of 4, and a frameshift gap penalty of 5.

Expression Systems

In order to use the fusion proteins described herein, it will generally be desirable to express them in a cell from a nucleic acid that encodes them. This can be performed in a variety of ways. For example, the nucleic acid encoding the fusion proteins can be cloned into a vector for transformation into prokaryotic or eukaryotic cells for replication and/or expression. Suitable vectors include prokaryote vectors, e.g., plasmids, or shuttle vectors, or insect vectors, for storage or manipulation of the nucleic acid encoding the fusion proteins. The nucleic acid encoding the fusion proteins can also be cloned into an expression vector, for expression in a plant cell, animal cell, preferably a mammalian cell or a human cell, fungal cell, bacterial cell, or protozoan cell.

To obtain expression, a sequence encoding a fusion proteins is typically subcloned into an expression vector that contains a promoter to direct transcription. Suitable bacterial and eukaryotic promoters are well known in the art and described, e.g., in Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 2010). Bacterial expression systems for expressing the engineered protein are available in, e.g., *E. coli, Bacillus* sp., and *Salmonella* (Palva et al., 1983, Gene 22:229-235). Kits for such expression systems are commercially available. Eukaryotic expression systems for mammalian cells, yeast, and insect cells are well known in the art and are also commercially available.

The promoter used to direct expression of a nucleic acid depends on the particular application. For example, a strong constitutive promoter is typically used for expression and purification of fusion proteins. In contrast, when the fusion proteins is to be expressed in vivo for gene regulation, either a constitutive or an inducible promoter can be used, depending on the particular use of the guide RNA. In addition, a preferred promoter for expression of the fusion proteins can be a weak promoter, such as HSV TK or a promoter having similar activity. The promoter can also include elements that are responsive to transactivation, e.g., hypoxia response elements, Gal4 response elements, lac repressor response element, and small molecule control systems such as tetracycline-regulated systems and the RU-486 system (see, e.g., Gossen & Bujard, 1992, Proc. Natl. Acad. Sci. USA, 89:5547; Oligino et al., 1998, Gene Ther., 5:491-496; Wang et al., 1997, Gene Ther., 4:432-441; Neering et al., 1996, Blood, 88:1147-55; and Rendahl et al., 1998, Nat. Biotechnol., 16:757-761).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the fusion proteins, and any signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the fusion proteins, e.g., expression in plants, animals, bacteria, fungus, protozoa, etc. Standard bacterial expression vectors include plasmids such as pBR322 based plasmids, pSKF, pET23D, and commercially available tag-fusion expression systems such as GST and LacZ.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include oMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

The vectors for expressing the fusion proteins can include RNA Pol III promoters to drive expression of the guide RNAs, e.g., the H1, U6 or 7SK promoters. These human promoters allow for expression of gRNAs in mammalian cells following plasmid transfection. Alternatively, a T7 promoter may be used, e.g., for in vitro transcription, and the RNA can be transcribed in vitro and purified.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with the fusion proteins encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., 1989, J. Biol. Chem., 264:17619-22; Guide to Protein Purification, in Methods in Enzymology, vol. 182 (Deutscher, ed., 1990)). Transformation of eukaryotic and prokaryotic cells are performed according to standard techniques (see, e.g., Morrison, 1977, J. Bacteriol. 132:349-351; Clark-Curtiss & Curtiss, Methods in Enzymology 101:347-362 (Wu et al., eds, 1983).

Any of the known procedures for introducing foreign nucleotide sequences into host cells may be used. These include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the fusion proteins.

The present invention includes the vectors and cells comprising the vectors, as well as cells expressing the fusion proteins described herein.

As an alternative to expressing the proteins in the cells, the proteins can be expressed, e.g., recombinantly, and then added to the cell (e.g., for methods that include contacting the cell with the proteins). A number of methods are known in the art for producing and purifying recombinant proteins.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of introducing a specific sequence into a target site on a double-stranded nucleic acid in a cell, the method comprising:
  contacting the cell with or expressing in the cell a donor nucleic acid molecule comprising the specific sequence to be inserted into the target nucleic acid; and
  contacting the cell with or expressing in the cell a nuclease that induces double stranded breaks (DSBs) only in specific phases of the cell cycle, comprising a fusion protein comprising a cell-cycle regulated protein domain linked to an engineered nuclease, wherein the cell-cycle regulated protein domain is selected from the group consisting of Cdk2, Cyclin A1, Cyclin A2, Cyclin B1, and Geminin (Gem) and the engineered nuclease is a CRISPR/Cas9 or a RFN.

2. The method of claim 1, wherein the fusion protein is selected from the group consisting of hGem-Cas9, Cas9-hGem, mAG-hGem-Cas9, Cas9-mAG-hGem, hGem-FokI-dCas9, hGem-mAG-FokI-dCas9, FokI-dCas9-hGem, FokI-dCas9-hGem-mAG, hGem-dCas9-FokI, hGem-mAG-dCas9-FokI, dCas9-FokI-hGem, and dCas9-FokI-hGem-mAG.

3. The method of claim 1, wherein the engineered nuclease comprises one or more nuclear localization signals and nuclear export signals, or nuclear-cytoplasmic shuttle sequences to control the trafficking of nuclease proteins into the cytoplasm.

4. The method of claim 1 further comprising expressing in the cell one or more guide RNAs that bind to or near the target site.

5. The method of claim 1, wherein the absolute rate of homology-directed repair (HDR) and/or the relative rate of HDR compared with non-homologous end joining (NHEJ) is improved.

6. The method of claim 1, wherein the double stranded DNA is genomic DNA.

7. A method of introducing a specific sequence into a target site on a double-stranded nucleic acid in a cell, the method comprising:
  contacting the cell with or expressing in the cell a donor nucleic acid molecule comprising the specific sequence to be inserted into the target nucleic acid; and
  contacting the cell with or expressing in the cell a nuclease that induces double stranded breaks (DSBs) only in specific phases of the cell cycle, comprising a fusion protein comprising a cell-cycle regulated protein domain linked to an engineered nuclease, wherein the cell-cycle regulated protein domain is Geminin (Gem) and the engineered nuclease is a CRISPR/Cas9 or a RFN.

8. The method of claim 7, wherein the fusion protein is selected from the group consisting of human Gemini (hGem)-Cas9, Cas9-hGem, mAG-hGem-Cas9, Cas9-mAG-hGem, hGem-FokI-dCas9, hGem-mAG-FokI-dCas9, FokI-dCas9-hGem, FokI-dCas9-hGem-mAG, hGem-dCas9-FokI, hGem-mAG-dCas9-FokI, dCas9-FokI-hGem, and dCas9-FokI-hGem-mAG.

9. The method of claim 7, wherein the engineered nuclease comprises one or more nuclear localization signals and nuclear export signals, or nuclear-cytoplasmic shuttle sequences to control the trafficking of nuclease proteins into the cytoplasm.

10. The method of claim 7 further comprising expressing in the cell one or more guide RNAs that bind to or near the target site.

11. The method of claim 7, wherein the absolute rate of homology-directed repair (HDR) and/or the relative rate of HDR compared with non-homologous end joining (NHEJ) is improved.

12. The method of claim 7, wherein the double stranded DNA is genomic DNA.

13. The method of claim 2, wherein the nuclease is fused to a catalytically inactive Csy4.

14. The method of claim 8, wherein the nuclease is fused to a catalytically inactive Csy4.

* * * * *

UNITED STATES PATENT AND TRADEMARK OFFICE
CERTIFICATE OF CORRECTION

Page 1 of 1

PATENT NO. : 11,021,718 B2
APPLICATION NO. : 15/516310
DATED : June 1, 2021
INVENTOR(S) : Joung et al.

It is certified that error appears in the above-identified patent and that said Letters Patent is hereby corrected as shown below:

In the Claims

In Column 38, Line 50 (approx.), Claim 8, delete "Gemini" and insert -- Geminin --

Signed and Sealed this
Eleventh Day of January, 2022

Drew Hirshfeld
*Performing the Functions and Duties of the
Under Secretary of Commerce for Intellectual Property and
Director of the United States Patent and Trademark Office*